US008617824B2

(12) United States Patent
Poetter et al.

(10) Patent No.: US 8,617,824 B2
(45) Date of Patent: Dec. 31, 2013

(54) ANALYTE DETECTION ASSAY

(75) Inventors: Karl Frederick Poetter, Northcote (AU); Edin Nuhiji, Geelong (AU); Paul Mulvaney, Alphington (AU)

(73) Assignees: Genera Biosystems Limited, Scoresby, Victoria (AU); The University of Melbourne, Parkville, Victoria (AU)

( * ) Notice: Subject to any disclaimer, the term of this patent is extended or adjusted under 35 U.S.C. 154(b) by 14 days.

(21) Appl. No.: 13/130,566

(22) PCT Filed: Nov. 20, 2009

(86) PCT No.: PCT/AU2009/001515
§ 371 (c)(1),
(2), (4) Date: Jul. 7, 2011

(87) PCT Pub. No.: WO2010/057264
PCT Pub. Date: May 27, 2010

(65) Prior Publication Data
US 2011/0256528 A1 Oct. 20, 2011

(30) Foreign Application Priority Data
Nov. 21, 2008 (AU) ................................ 2008906057

(51) Int. Cl.
*G01N 33/53* (2006.01)
*G01N 33/543* (2006.01)
*G01N 33/532* (2006.01)

(52) U.S. Cl.
USPC ............ 435/7.1; 435/7.92; 436/523; 436/544

(58) Field of Classification Search
None
See application file for complete search history.

(56) References Cited

U.S. PATENT DOCUMENTS

| 7,259,855 B2 | 8/2007 | Fan et al. |
| 7,384,797 B1 | 6/2008 | Blair |
| 2002/0097401 A1 | 7/2002 | Maleki et al. |

FOREIGN PATENT DOCUMENTS

WO    WO 2005/116615 A1    12/2005

OTHER PUBLICATIONS

Supplemental European Search Report for European Application No. EP 09 82 7053, dated Jul. 23, 2012.
Vollmer, F. et al. 2003 "Multiplexed DNA quantification by spectroscopic shift of two microsphere cavities" *Biophysical Journal* 85: 1974-1979.
Vollmer, F. and Arnold, S. 2008 "Wispering-gallery-mode biosensing: label-free detection down to single molecules" *Nature Methods* 5: 591-596.
Gomez, D.E., et al. 2005 "Tunable whispering gallery mode emission from quantum-dot-doped microspheres" *Small* 1(2): 238-241.
Nuhiji, E. and Mulvaney, P. 2007 "Detection of unlabeled oligonucleotide targets using whispering gallery modes in single, fluorescent microspheres" *Small* 3(8): 1408-1414.
Rakovich, Y.P. et al. 2003 "Raman scattering and anti-stokes emission from a single spherical microcavity with a CdTe quantum dot monolayer" *Applied Physics Letters* 83: 2539-2541.
Sigma-Aldrich, Retrieved from the internet at <http://www.sigmaaldrich.com/etc/medialib/docs/Sigma/General_Information/2/biofiles_issues10.Par.0001.File.tmp/biofiles_issue10.pdf. on Jan. 25, 2010, "Fluorescent Microparticles and Nanobeads," Biofiles for Life Science Research, vol. 2(5) 2007 (Sigma-Aldrich,), pp. 25-27.

*Primary Examiner* — Shafiqul Haq
(74) *Attorney, Agent, or Firm* — Knobbe, Martens, Olson & Bear, LLP

(57) ABSTRACT

A rapid and sensitive analyte detection assay is based on whispering gallery modes of fluorescently labelled microspheroidal particles. Ligands for the analyte, such as nucleic acids, are anchored to the particles. The fluorescent labels may comprise fluorophores or quantum dots. In the latter case, the particles may comprise melamine formaldehyde. The assay may be used to detect analytes in aqueous samples.

17 Claims, 18 Drawing Sheets

ANALYTE DETECTION ASSAY

FILING DATA

This application is associated with and claims priority from Australian Provisional Patent Application No. 2008906057, filed on 21 Nov. 2008, entitled "Analyte detection assay", the entire contents of which, are incorporated herein by reference.

FIELD

The present invention relates to the field of analyte detection. More particularly, the present invention relates to biosensing and rapid and sensitive analyte detection using a whispering gallery mode (WGM)-based assay.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

The circular optical modes in monolithic resonators are referred to as "whispering gallery modes" (WGM) or "morphology dependent resonances" (MDR). such modes or resonances are closed trajectories of light (standing light waves) supported by total internal reflections from the boundaries of a resonator. A WGM occurs when standing light waves of a particular emission profile are confined by a near-total internal reflection inside the surface of a spherical dielectric cavity (Moller et al, *Applied Physics Letters* 83(13):2686-2688, 2003).

The WGM technology is described in detail in International Patent Publication No. WO 2005/116615, which is incorporated herein by reference. WGM technology is predicated, in part, on the phenomenon that fluorophores enable a distinctive WGM profile to be generated. The fluorophores are incorporated onto quantum dots which are into the microparticles by diffusion or may be incorporated during their manufacture. The type of fluorophore is unlimited and may for example be an organic dye, a rare earth based lumophore, a semiconductor nanocrystal of various morphologies and compositions. a phosphor or other material which emits light when illuminated. This fluorophore or mixture thereof is then attached to microspheroidal particles. When a target analyte interacts with a binding partner immobilized to the microspheroidal particle, the WGM profile changes, enabling detection of the binding event.

WGM allow only certain wavelengths of light to be emitted from the particle. The result of this phenomenon is that the usual broad emission (10-100 nm wide) bands from, for example, a fluorophore, become constrained and appear as a series of sharp peaks corresponding effectively to standing mode patterns of light within the particle. The WGM profile is extremely sensitive to changes at the surface of the microspheroidal particle and the WGM profile changes when the microspheroidal particle interacts with analytes or molecules within its environment.

The detection of rare analytes in samples of diverse origin requires a sensitive, versatile and practical detection means. There is a necessity to devise methods to increase sensitivity, versatility and practicality of WGM for the detection of analytes.

SUMMARY

The present invention provides a sensitive method and reagents based on whispering gallery mode (WGM) detection assays, for, inter alia, detecting analytes in a sample.

In particular, it is the aim of the present invention to describe a method by which unlabeled analytes may be routinely detected in any medium (liquid or gas) by exploiting the sensitivities of WGMs to the environment. Reference to liquid and gas includes aqueous solutions and biological buffers and air.

The method and reagents of the present invention are predicated, in one part, on the unexpected determination that the coating of microspheres with a fluorophore per se, as opposed to using discrete quantum dots, enhances the sensitivity of the WGM-based detection. In another part, the selection of particle such as a particle with functionalized chemical groups on its surface increases sensitivity when either quantum dots or direct fluorophore coating occurs. In yet another part, the particle is selected having a higher refractive index relative to the medium in which the assay is conducted. In an embodiment, the microspheroidal particle has a refractive index greater than 1.40.

Accordingly, one aspect of the present invention provides a method of analyte detection in a medium, the method comprising subjecting microspheres coated with a fluorophore and a multiplicity of ligands to WGM detection means to identify a binding event between one or more ligands and a ligand binding analyte.

In another aspect the present invention provides a method of analyte detection in a medium, the method comprising subjecting microspheres wherein the microspheres have a higher refractive index than the medium comprising the analyte coated with a fluorophore and a multiplicity of ligands to WGM detection means to identify a binding event between one or more ligands and a ligand binding analyte. In an embodiment, the microspheroidal particle has a refractive index greater than 1.40.

Another aspect of the present invention provides a method for detecting a binding event between an analyte and a ligand, comprising the steps of: (i) anchoring a multiplicity of ligands to a population of fluorophore-conjugated microspheroidal particles; (ii) contacting the microspheroidal particles with a negative control sample and determining a baseline spectrum; (iii) contacting the microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

Another aspect of the invention comprises, a method for detecting an analyte in a medium, comprising the steps of:

(i) anchoring a multiplicity of ligands to the analyte to a population of fluorophore-conjugated microspheroidal particles wherein if the microspheroidal particle is melamine formaldehyde then it may be conjugated with the fluorophore or comprise a quantum dot;

(ii) contacting the microspheroidal particles with a negative control sample and determining a baseline spectrum;

(ii) contacting the microspheroidal particles with a sample putatively comprising the analyte for a time and under conditions sufficient to facilitate a binding event between the analyte and its respective ligand; and (iii) subjecting the microspheroidal particles to whispering gallery modes (WGM) detection means to detect a binding event.

In a particular embodiment, the microspheroidal particles are functionalized by chemical moieties such as with azide, alkyne, amine, aldehyde, sulfate or thiol, carboxyl, carboxylate and/or hydroxyl groups. In one aspect, the microspheroidal particles are amine-aldehyde particles such as but not limited to melamine particles or melamine formaldehyde particles.

Hence, another aspect of the present invention provides a method for detecting a binding event between an analyte and a ligand, comprising the steps of: (i) anchoring a multiplicity of ligands to a population of fluorophore-conjugated functionalized microspheroidal particles; (ii) contacting the functionalized microspheroidal particles with a negative control sample and determining a baseline spectrum; (iii) contacting the functionalized microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

In a particular embodiment, the present invention provides a method for detecting a binding event between an analyte and a ligand, comprising the steps of: (i) anchoring a multiplicity of ligands to a population of fluorophore-conjugated amine-aldehyde microspheroidal particles; (ii) contacting the amine-aldehyde microspheroidal particles with a negative control sample and determining a baseline spectrum; (iii) contacting the amine-aldehyde microspheroidal particles with a sample putatively comprising the analyte for a time and under conditions sufficient to facilitate a binding event between the analyte and its respective ligand; and (iv) subjecting the amine-aldehyde microspheroidal particles to WGM detection means to detect a binding event.

In a most particular embodiment, the amine-aldehyde particles are melamine formaldehyde particles.

Hence, the present invention provides a method for detecting a binding event between an analyte and a ligand, comprising the steps of: (i) anchoring a multiplicity of ligands to a population of fluorophore-conjugated melamine formaldehyde microspheroidal particles; (ii) contacting the melamine formaldehyde microspheroidal particles with a negative control sample and determining a baseline spectrum; (iii) contacting the melamine formaldehyde microspheroidal particles with a sample putatively comprising the analyte for a time and under conditions sufficient to facilitate a binding event between the analyte and its respective ligand; and (iv) subjecting the melamine formaldehyde microspheroidal particles to WGM detection means to detect a binding event.

When the particles are melamine formaldehyde, the particles may also comprise quantum dots. Hence, another aspect of the present invention provides a method for detecting a binding event between an analyte and a ligand, comprising the steps of: (i) anchoring a multiplicity of ligands to a population of melamine formaldehyde microspheroidal particles comprising fluorophore-coated quantum dots; (ii) contacting the microspheroidal particles with a negative control sample and determining a baseline spectrum; (iii) contacting the microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

Another aspect of the present invention provides a method for detecting a binding event between an analyte and a ligand, comprising the steps of: (i) anchoring a multiplicity of ligands to a population of microspheroidal particles having a higher refractive index than the medium comprising the analyte, the microspheroidal particles encoding a fluorophor; (ii) contacting the microspheroidal particles with a negative control sample and determining a baseline spectrum; (iii) contacting the microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

Yet another aspect of the present invention provides a method of detecting an analyte, the method comprising contacting at least one population of microspheroidal particles with a sample putatively comprising the analyte, wherein each particle within a population of microspheroidal particles comprises a fluorophore which emits visible radiation in response to infrared excitation and an immobilized putative binding partner of the analyte wherein each particle population has a defined WGM profile, wherein binding of the analyte to the immobilized binding partner results in a change in the WGM profile of the at least one population of microspheroidal particles which is indicative of the presence of the analyte.

In one embodiment, the analyte or its respective ligand comprises a molecule selected from the list consisting of: nucleic acid; protein; peptide; antibody; lipid; carbohydrate; and any small molecule or chemical entity. including cells (e.g. cancer cells), bacteria and viruses.

In a specific embodiment, the ligands anchored to the microspheroidal particles are nucleic acid molecules and the analytes to be detected are complementary nucleic acid molecules.

In another embodiment, the nucleic acid ligand or analyte is a DNA molecule comprising a single-stranded DNA sequence.

Another aspect of the present invention provides the use of a method comprising the steps of: (i) anchoring a multiplicity of ligands to a population of fluorophore-conjugated microspheroidal particles; (ii) contacting the microspheroidal particles with a negative control sample and determining a baseline spectrum; (iii) contacting the microspheroidal particles with a sample putatively comprising the analyte for a time and under conditions sufficient to facilitate a binding event between the analyte and its respective ligand; and (iv) subjecting the microspheroidal particles to WGM detection means in the manufacture of an assay to detect a binding event between an analyte and a ligand.

In a further embodiment, the microspheres may be recycled. In addition, the assay may be conducted in any medium such as air or other gas or in a liquid phase such as an aqueous solution, biological buffer or complex biological fluid.

In yet another aspect the present invention provides a kit comprising fluorophore-conjugated microspheroidal particles and a multiplicity of ligands for anchoring thereto, for detecting a binding event between a ligand and an analyte by WGM detection means.

In a specific embodiment, the kit comprises fluorophore-conjugated microspheroidal particles to which a multiplicity of ligands has been attached. When the particles are melamine formaldehyde, the fluorophore may be coated on an organic dye or a quantum dot.

In a further aspect the present invention provides a biosensor comprising WGM detection means wherein the biosensor is a self-contained unit comprising a power source, light source, sample-handling chamber and a spectrophotometer.

Nucleotide and amino acid sequences are referred to by a sequence identifier number (SEQ ID NO). The SEQ ID NOs correspond numerically to the sequence identifiers <400>1

(SEQ ID NO:1), <400>2 (SEQ ID NO:2), etc. A summary of the sequence identifiers is provided in Table 1. A sequence listing is provided after the claims.

A summary of sequence identifiers used throughout the subject specification is provided in Table 1.

TABLE 1

Summary of sequence identifiers

| SEQUENCE ID NO: | DESCRIPTION |
|---|---|
| 1 | oligonucleotide - en1 |
| 2 | oligonucleotide - α-en1 |
| 3 | oligonucleotide - 40 base α-en1 |
| 4 | oligonucleotide - 20 base α-en1 |
| 5 | oligonucleotide - 10 base α-en1 |
| 6 | oligonucleotide - Control (random non-specific target sequence) |
| 7 | Human SNP target DNA sequence - rs10434 |
| 8 | Human rs10434 SNP complementary DNA probe sequence - α-rs10434 A |
| 9 | Human rs10434 SNP mismatch DNA probe sequence - α-rs10434 B |
| 10 | Human rs10434 SNP region |
| 11 | Forward Primer |
| 12 | Reverse Primer |

BRIEF DESCRIPTION OF THE FIGURES

Some figures contain color representations or entities. Color photographs are available from the Patentee upon request or from an appropriate Patent Office. A fee may be imposed if obtained from a Patent Office.

DETAILED DESCRIPTION

Figure 1:
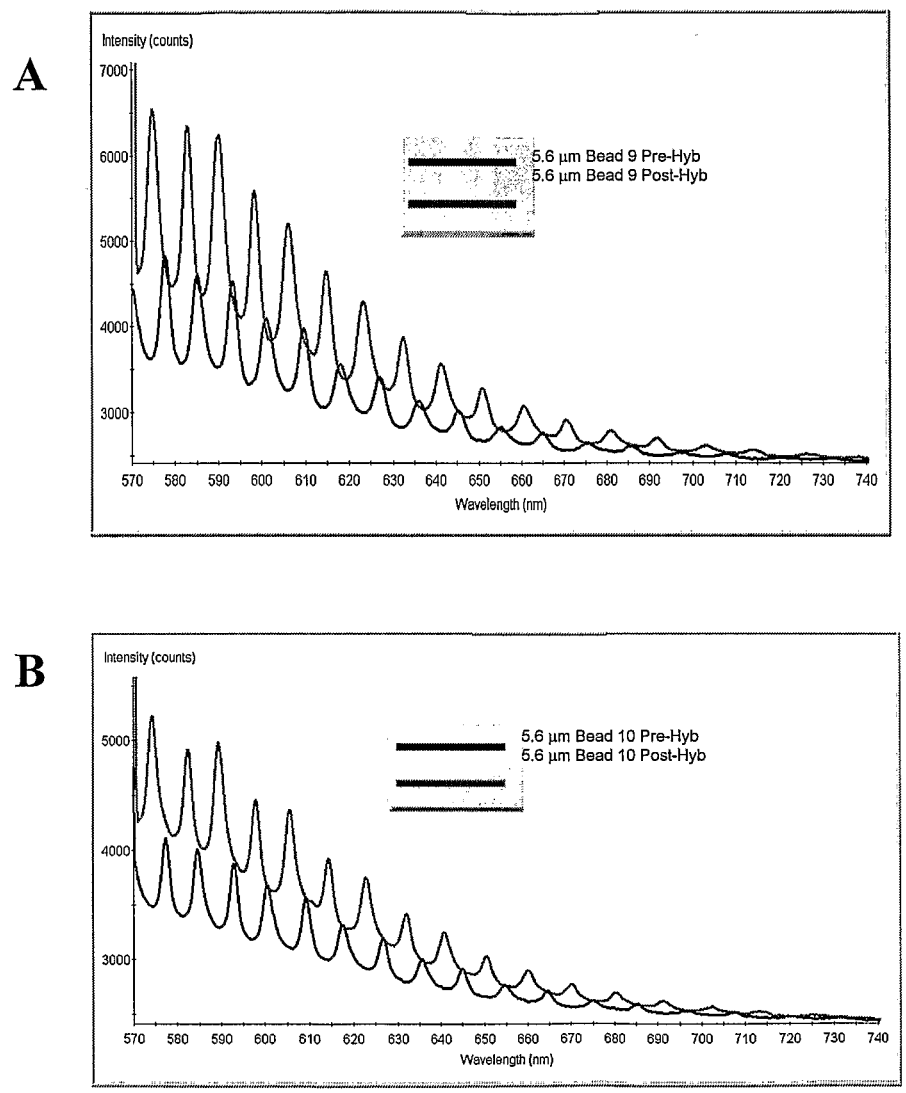
FIG. 1 is a graphical representation of WGM DNA biosensing demonstrating consistent and measurable shifts after binding. These measurements have been carried out in an aqueous solution containing pH buffers and an electrolyte. A demonstrable shift in WGM profile was observed for each of beads 9, 10, 11 and 12 (A, B, C and D respectively) after the beads or microspheroidal particles were contacted with a nucleic acid analyte complementary to the nucleic acid analyte-binding partner anchored to the surface of the beads. Each of the beads was 5.6 μm in diameter.
Figure 1:
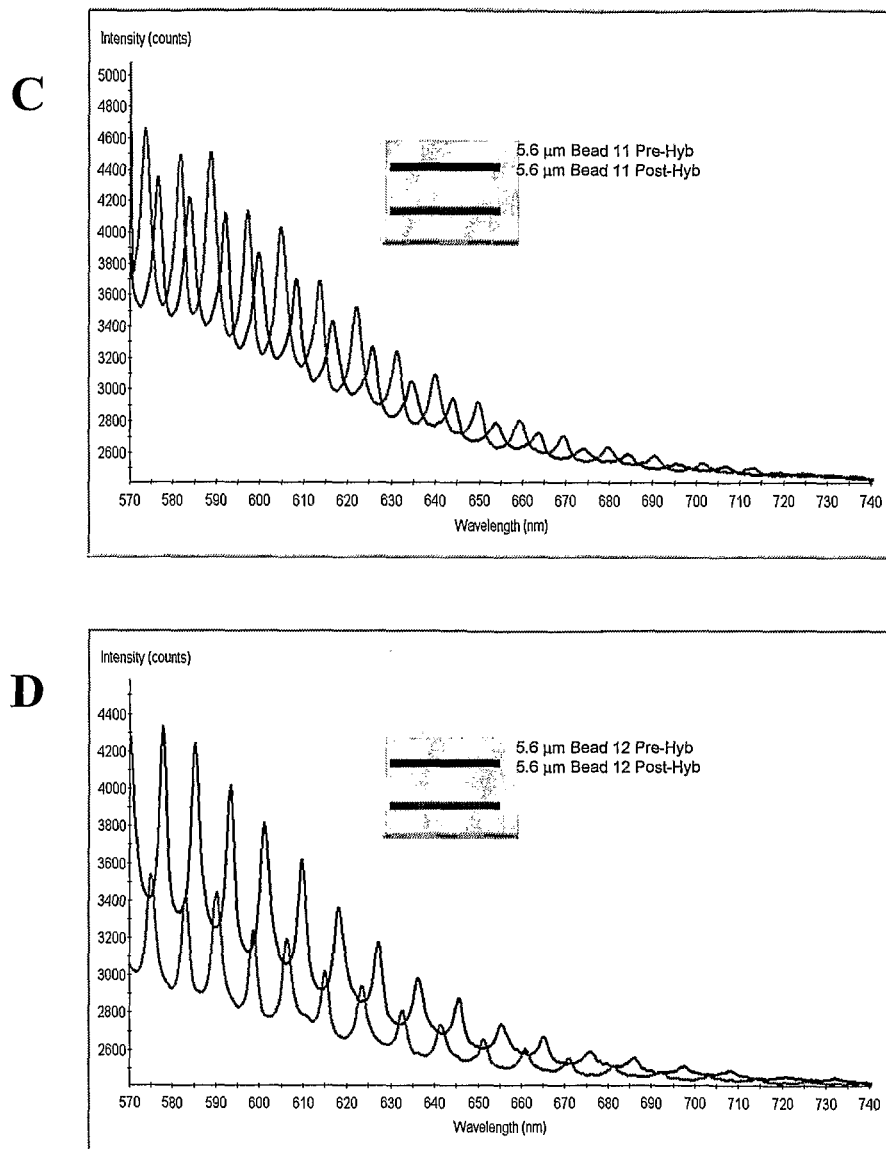

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used in the subject specification, the singular forms "a", "an" and "the" include plural aspects unless the context clearly dictates otherwise. Thus, for example, reference to "a ligand" includes a single ligand, as well as two or more ligands; reference to "an analyte" includes a single analyte, as well as two or more analytes; reference to "the fluorophore" includes a single fluorophore, as well as two or more fluorophores; reference to "the invention" includes single or multiple aspects of an invention; and so forth.

The present invention provides a multiplicity of analyte-binding partners or ligands conjugated to fluorophore-coated microspheroidal particles. When these particles are illuminated, a "baseline" whispering gallery modes (WGM) spectrum or profile is emitted. Each population of microspheroidal particles has a unique WGM baseline signature. This baseline profile is altered by binding of analytes to the analyte-binding partner or ligand on the surface of the microspheroidal particles, causing a detectable shift in the WGM spectrum.

The microspheroidal particles of the present invention comprise microspheres coated with fluorophores, which, when illuminated, emit fluorescent light. The emitted light is trapped within the microsphere and resonates within the sphere creating a spectrum of discrete wavelengths termed whispering gallery modes or "WGM". The coating of the microspheroidal particles with a fluorophore as opposed to using discrete quantum dots enhances the sensitivity of WGM-based detection. The present invention extends to microspheroidal particles coated with a fluorophore (i.e. without using quantum dots) or the use of quantum dots in combination with melamine formaldehyde particles. The microspheroidal particles may also be selected on the basis that they have a higher refractive index relative to the medium comprising the analyte. In an embodiment, the microspheroidal particle has a refractive index greater than 1.40.

As used herein, the term "quantum dot" or "QD" is to be understood as encompassing particles known in the art as semiconductor nanoparticles, nanocrystals, quantum dots, or Qparticles.

The term "microspheroidal particles" and "microspheres" are used interchangeably herein and include spherical particles comprising any material, homogenous or otherwise which can produce one or more WGM profiles based on its fluorophore. As will be evident to those of skill in the art, almost any material, homogenous or otherwise, may be used for the microspheroidal particle. The microspheroidal particles contemplated herein may also comprise more than one substance, and as such may comprise shells, alloys or mixtures of organic and/or inorganic substances. It is advantageous for quantification of the data generated by the methods of the present invention if the microspheroidal particle comprises a substantially homogenous material with an isotropic refractive index and which is also non-absorbing (other than the fluorophore, which is further described below).

The microspheroidal particles of the present invention comprise a material selected from the list consisting of: melamine or a chemical derivative thereof such as melamine formaldehyde; silica; latex; titania; tin dioxide; yttria; alumina; other binary metal oxides; perovskites and other piezo-electric metal oxides; PLGA; sucrose; agarose; and other polymers.

In a particular embodiment, the microspheroidal particles are functionalized by chemical moieties such as with amine, aldehyde, sulfate or thiol, carboxyl, carboxylase and/or hydroxyl groups. In one aspect, the microspheroidal particles are amine-aldehyde particles such as but not limited to melamine formaldehyde (MF) particles. MF particles provide a robust conjugation substrate for acryloyl modified target oligonucleotides and proteins to bind. The covalent bond remains intact after exposure to high pH solutions and extreme temperatures, as a high quality WGM can acquire post-treatment.

Melamine is a trimer of cyanamide and is also known as: 1,3,5-triazine-2,4,6-triamine; 2,4,6-triamino-s-triazine; cyanurotriamide; cyanurotriamine or cyanuramide. In a particular embodiment, the melamine is melamine formaldehyde.

The present invention also extends to the use of magnetic particles in the WGM assay. Such particles could be presented in very precise fixed positions. Magnetic facilitated particle immobilization enables discrete single particle analysis and alleviates the need to fabricate custom immobilization substrates.

In a particular embodiment, high refractive index particles are selected which support WGM in solution such as colloidal silica, zirconia or titania. Alternatively, microspheres shelled with higher refractive index materials provide useful ideal sensor platform. These particles contain high order radial modes within the adsorbed layer and as a result should enable the acquisition of high Q WGM spectra which contain the high order modes.

Employing semiconductor nanocrystals (e.g. CdSe, CdTe, CdS) provides another fluorescently robust alternative. A fluorescently stable particle which supports WGM in solution may be produced by the adsorption of a monolayer of nanocrystals to a homogenous microsphere followed by a stabilizing high refractive index shell. A list of commercially available high refractive index materials and particles is provided below.

The term fluorophore is general and is not limited to organic dyes, but includes any chemical, molecule or material, which has the property of emitting light of a well defined wavelength when illuminated. This includes but is not restricted to; organic dyes, organometallic complexes, quantum dots (including nanorods, nanowires and other morphologies, coated and uncoated QDs, alloys and mixtures thereof), rare earth ions or mixtures thereof, upconverters and also infra-red emitting fluorophores, which may be advantageous in absorbing samples. Other materials may also be incorporated such as defective fluorescent materials such as diamond containing Nitrogen induced defects or vacancies.

WGMs may be generated by fluorophores that are attached to the surface of the microsphere, but may also be generated when the fluorophore is embedded or distributed within the microsphere. The distribution of fluorophores affects the intensity of different modes of the WGM, but for the purposes of this invention, no distinction is made between fluorophores that are on the surface or within the microsphere.

| Metals |
| --- |
| Titania $TiO_2$ (2.20), Aluminium $Al_2O_3$ (1.77), Mylar (1.65), Copper Cu (2.43), Platinum Pt (2.33) |
| Minerals (gemstones) |
| Diamond (2.42), Quartz (1.54-1.55), Ruby (1.76-1.78), Sapphire (1.76-1.78), Sapphire Star (1.76-1.77), Spessarite (1.79-1.81), Spinel (1.72-1.73), Spinel Blue (1.72-1.74), Spinel Red (1.71-1.74), Star Ruby (1.76-1.77), Tanzanite (1.69-1.70), Topaz (1.61-1.63), Crystal (2.00) |
| Plastics |
| Melamine Formaldehyde Resin $(C_5H_8N_6O)_n$ [not to be confused with melamine] (1.68), is made from the polymerization process of melamine with formaldehyde |
| Ceramics |
| Ceramic Zirconia Silicate (2.00-2.20), Zirconia $ZnO_2$ (2.40) |
| Glass |
| High refractive index glass (2.00), Fused Silica (quartz 1.46), Glass Pyrex (1.47), Plexiglas (1.48) |
| Common Transparent Materials |
| Lucite (1.49) |

The present invention is predicated, in part, on the determination that WGM detection means do not require microspheres to be coated with quantum dots.

Accordingly, one aspect of the present invention provides a method of analyte detection in a medium, the method comprising subjecting microspheres coated with a fluorophore and a multiplicity of ligands to WGM detection means to identify a binding event between one or more ligands and a ligand binding analyte.

In another aspect the present invention provides a method of analyte detection in a medium, the method comprising subjecting microspheres wherein the microspheres have a higher refractive index than the medium comprising the analyte coated with a fluorophore and a multiplicity of ligands to WGM detection means to identify a binding event between one or more ligands and a ligand binding analyte.

Another aspect of the present invention provides, a method for detecting an analyte in a medium, comprising the steps of:

(i) anchoring a multiplicity of ligands to the analyte to a population of fluorophore-conjugated microspheroidal particles wherein if the microspheroidal particle is melamine formaldehyde then it may be conjugated with the fluorophore or comprise a quantum dot;

(ii) contacting the microspheroidal particles with a negative control sample and determining a baseline spectrum;

(ii) contacting the microspheroidal particles with a sample putatively comprising the analyte for a time and under conditions sufficient to facilitate a binding event between the analyte and its respective ligand; and (iii) subjecting the microspheroidal particles to whispering gallery modes (WGM) detection means to detect a binding event.

Reference to "coated" or "conjugated" should be understood as reference to the incorporation of a fluorophore onto the surface of a microspheroidal particle without the aid of a quantum dot or its functional equivalent.

As used herein, the term "fluorophore" refers to any molecule which exhibits the property of fluorescence. For the purposes herein, the term "fluorescence" may be defined as the property of a molecule to absorb light of a particular wavelength and re-emit light of a longer wavelength. The wavelength change relates to an energy loss that takes place in the process. The term "fluorophore" may encompass a range of fluorophores such as chemical fluorophores and dyes.

The fluorophore may be chosen to emit at any wavelength at which WGM profile may be easily resolved. This depends on the ratio of the wavelength of the emission to the particle radius. Given that the sphere radius is arbitrary, the emission may be suitably chosen from the ultraviolet (wavelength range of about 350 nm to about 3 nm), visible (wavelength range of about 350 nm to about 800 nm), near infrared ([NIR]) (wavelength range of about 800 nm to about 1500 nm) and/or infrared ([IR]) (wavelength range of about 1500 nm to about 10 µm) ranges. However, due to the ease of detection, in one particularly preferred embodiment, the fluorophore is detectable in the visible wavelength range.

In one particular embodiment, the fluorophore emits visible radiation in response to Infrared excitation. Such fluorophores are also referred to herein as "upconverters".

Accordingly, another aspect of the present invention provides a method of detecting an analyte, the method comprising contacting at least one population of microspheroidal particles with a sample putatively comprising the analyte, wherein each particle within a population of microspheroidal particles comprises a fluorophore which emits visible radiation in response to infrared excitation and an immobilized putative binding partner of the analyte wherein each particle population has a defined WGM profile, wherein binding of the analyte to the immobilized binding partner results in a change in the WGM profile, when compared to the baseline WGM profile, of at least one population of microspheroidal particles which is indicative of the presence of the analyte.

In a particular embodiment, the microspheroidal particles are functionalized by chemical moieties such as with amine, thiol and/or aldehyde groups, sulfate, carboxylate, hydroxyl groups, axide and/or alkynes. Furthermore, amine-aldehyde-based particles such as melamine formaldehyde, provide a usefuls substrate for acryloyl modified target oligonucleotides and proteins to bind.

Hence, another aspect of the present invention provides a method for detecting a binding event between an analyte and a ligand, comprising the steps of: (i) anchoring a multiplicity of ligands to a population of fluorophore-conjugated functionalized microspheroidal particles; (ii) contacting the functionalized microspheroidal particles with a negative control sample and determining a baseline spectrum; (iii) contacting the functionalized microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

In a particular embodiment, the present invention provides a method for detecting a binding event between an analyte and a ligand, comprising the steps of: (i) anchoring a multiplicity of ligands to a population of fluorophore-conjugated amine-aldehyde microspheroidal particles; (ii) contacting the amine-aldehyde microspheroidal particles with a negative control sample and determining a baseline spectrum; (iii) contacting the amine-aldehyde microspheroidal particles with a sample putatively comprising the analyte for a time and under conditions sufficient to facilitate a binding event between the analyte and its respective ligand; and (iv) subjecting the amine-aldehyde microspheroidal particles to WGM detection means to detect a binding event.

In a most particular embodiment, the amine-aldehyde particles are melamine formaldehyde. Hence, the present invention provides a method for detecting a binding event between an analyte and a ligand, comprising the steps of: (i) anchoring a multiplicity of ligands to a population of fluorophore-conjugated melamine formaldehyde microspheroidal particles; (ii) contacting the melamine formaldehyde microspheroidal particles with a negative control sample and determining a baseline spectrum; (iii) contacting the melamine formaldehyde microspheroidal particles with a sample putatively comprising the analyte for a time and under conditions sufficient to facilitate a binding event between the analyte and its respective ligand; and (iv) subjecting the melamine formaldehyde microspheroidal particles to WGM detection means to detect a binding event.

When the particle is melamine formaldehyde, quantum dots may also be used.

Hence, another aspect of the present invention provides a method for detecting a binding event between an analyte and a ligand, comprising the steps of: (i) anchoring a multiplicity of ligands to a population of melamine formaldehyde microspheroidal particles comprising fluorophore-coated quantum dots; (ii) contacting the microspheroidal particles with a negative control sample and determining a baseline spectrum; (iii) contacting the microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

Another aspect of the present invention provides a method for detecting a binding event between an analyte and a ligand, comprising the steps of: (i) anchoring a multiplicity of ligands to a population of microspheroidal particles having a higher refractive index than the medium comprising the analyte, the microspheroidal particles encoding a fluorophor; (ii) contacting the microspheroidal particles with a negative control sample and determining a baseline spectrum; (iii) contacting the microspheroidal particles with a sample putatively comprising the analyte for a time and under conditions sufficient to facilitate a binding event between the analyte and its respective ligand; and (iv) subjecting the microspheroidal particles to WGM detection means to detect a binding event.

The only constraints on the fluorophore is that the emission should result in cavity mode emission, and the fluorophores of the present invention specifically exclude quantum dots.

There are many fluorescent dyes which are available in the art which may be used as fluorophores in accordance with the present invention. An important property of a fluorescent dye or other fluorophore, which determines its potential for use is the excitation wavelength of the fluorophore; it must match the available wavelengths of the light source. However, many different fluorescent dyes and other fluorophores will be familiar to those of skill in the art, and the choice of fluorescent marker in no way limits the subject invention.

Convenient "fluorophores" which may be used for the labeling of a microspheroidal particle comprise any fluorescent marker which is excitable using a light source selected from the group below:

(i) Argon ion lasers—comprise a blue, 488 nm line, which is suitable for the excitation of many dyes and fluorochromes that fluoresce in the green to red region. Tunable argon lasers are also available that emit at a range of wavelengths (458 nm, 488 nm, 496 nm, 515 nm amongst others).

(ii) Diode lasers—have an emission wavelength of 635 nm. Other diode lasers which are now available operate at 532 nm. This wavelength excites propidium iodide (PI) optimally. Blue diode lasers emitting light around 476 nm are also available. Such diode lasers may be conveniently employed to excite WGMs within the microspheroidal particles.

(iii) HeNe gas lasers—operate with the red 633 nm line. Such lasers may be conveniently employed to excite WGMs within the microspheroidal particles.

(iv) Light Emitting Diodes (LEDs)

(v) HeCd lasers—operate at 325 nm. Such lasers may be conveniently employed to excite WGMs within the microspheroidal particles.

(vi) 100 W mercury arc lamp—the most efficient light source for excitation of UV dyes like Hoechst and DAPI.

(vii) Xe arc lamps and quartz halogen lamps—may be used as a means to excite WGMs and hence utilize the particles as sensors.

In a particular embodiment of the present invention, the fluorescent markers are selected from: Alexa Fluor dyes; BoDipy dyes, including BoDipy 630/650 and BoDipy 650/665; Cy dyes, particularly Cy3, Cy5 and Cy 5.5; 6-FAM (Fluorescein); Fluorescein dT; Hexachlorofluorescein (HEX); 6-carboxy-4',5'-dichloro-2',7'-dimethoxyfluorescein (JOE); Oregon green dyes, including 488-X and 514; Rhodamine dyes, including Rhodamine Green, Rhodamine Red and ROX; Carboxytetramethylrhodamine (TAMRA); Tetrachlorofluorescein (TET); and Texas Red.

Two dyeing techniques, internal dyeing and external dyeing (surface-labeling), are commonly used to fluorescently label microspheroidal particles. The two techniques produce particles with unique properties, each beneficial for different applications. Internal dyeing produces extremely stable particles with typically narrow fluorescence emissions. These particles often display a greater resistance to photobleaching. As the fluorophore is inside the particles, surface groups are available for use in conjugating ligands (proteins, antibodies, nucleic acids, etc.) to the surface of the bead. For this reason, internally labeled particles are typically used in analyte-detection and immunoassay applications. Surface-labeling involves conjugation of the fluorophore to the microspheroidal particle surface. Because the fluorophores are on the surface of the particle, they are able to interact with their environment just as the fluorophores on a stained cell. The result is a particle standard that exhibits the same excitation and emission properties as stained cell samples, under a variety of different conditions, such as the presence of contaminants or changes in pH. The "environmentally responsive" nature of surface-labeled particles makes them ideally suited for mimicking biological samples. Externally labeled particles are frequently used as controls and standards in a number of applications utilizing fluorescence detection. However, the present invention contemplates the association of a particle with a fluorescent label via any means.

As used herein, the term "fluorophore" should be understood to also encompass multiple fluorophores, and mixtures of fluorophores. The use of all such fluorophores on microspheroidal particles is to be considered as being within the scope of the methods and reagents described herein.

In accordance with the present invention, it has been shown that the emission of any particular fluorophore depends on the distribution of the fluorophore in the microspheroidal particle, the type of fluorophore and the concentration of fluorophore. However, the methods of the present invention are still practicable irrespective of whether the fluorophore is at the surface of the microspheroidal particle, present as a shell within the microspheroidal particle, located at the core of the microspheroidal particle or is present in more than one of the recited locations.

It should be noted that the methods of the present invention are not predicated on quenching of the emission from the fluorophore. The methods of the present invention, however, are predicated, in part, on a modulation (i.e. a change) in the WGM profile of the fluorophore as a result of an interaction or association of an analyte with a binding partner immobilized to the surface of a microspheroidal particle.

WGM, when dealing with electromagnetic radiation, are electromagnetic resonances that can be established when incident light interacts with a particle of higher refractive index than its surrounding medium. WGM occur at particular resonant wavelengths of light for a given particle size, and the nature of the WGM may change with, inter alia, the size of the particle containing the WGM and the refractive indices of both the particle and the surrounding medium. Furthermore, the size of the particle can also affect the WGM established therein. WGM are established when the incident light undergoes total internal reflection at the particle surface.

Total internal reflection (TIR) may occur at the interface between two non-absorbing media. When a beam of light propagating in the medium of higher refractive index meets an interface at a medium of lower refractive index at an angle of incidence above a critical angle, the light is totally reflected at the interface and propagates back into the high refractive index medium. As will be evident to a person skilled in the art, in a 3-dimensional medium the light may be reflected many times within the particle of higher refractive index. In a WGM, the light is concentrated near the circumference of the particle and can be assigned a mode number and a mode order. The mode number, n, provides the number of wavelengths around the circumference of the particle, and the mode order, l, provides the number of maxima in the radial dependence of the electromagnetic field within the particle.

Fluorescence emitters embedded on a particle, as defined herein, display defined WGM profiles. These modes allow only certain wavelengths of light to be emitted from the particle. The result of this phenomenon is that the usual relatively broad emission spectrum of a fluorophore (for example, fluorophores typically emit in a 10-100 nm wide band) becomes constrained and appears as a series of sharp "peaks" corresponding effectively to standing mode patterns of light within the particle. The series of peaks generated as a result of the establishment of a WGM in the microspheroidal particle of the present invention are referred to herein as "whispering gallery mode profiles" or "WGM profiles".

The WGM profile is extremely sensitive to both the position of the embedded fluorophore and their concentration and spatial configuration with respect to each other. Particle size and refractive index are the 2 most important parameters in determining the emission wavelengths seen in a WGM profile.

It is proposed that the position and amplitude of one or more peaks in a WGM profile may be strongly influenced by interactions or associations of the microspheroidal particle with molecules in a sample or external environment.

In one example, association or binding of a molecule to a microspheroidal particle alters the effective refractive index of the microspheroidal particle altering the WGM profile generated by the microspheroidal particle.

Any number of means known in the art are suitable for conjugating fluorophores to the surface of microspheres. Microsphere surfaces can be optimized or functionalized for hydrophobic adsorption or covalent attachment of molecules including fluorophores or any biological or chemical molecule. The present invention does not extend to and specifically excludes the use of quantum dots to label the microspheres.

The surface of microspheres can be functionalized by the addition of any number of functional groups including: azide, alkyne, maleimide, succinimide, epoxide, methacrylate, acryloyl, amine, aldehyde, sulfate or thiol; carboxyl; carboxylate; hydroxyl; etc.

In one embodiment, nucleic acid molecules are bound covalently to a sulfur-coated surface of a silica microsphere. Silanization with 3-mercaptopropyltrimethoxysilane followed by exhaustive washing is used to create this surface. Nucleic acid molecules, for example, DNA oligonucleotides, are manufactured with 5' thiol or acryl groups and are attached to the free sulfurs on the surface.

The ligands of the present invention are in no way limited to any one species and include ligands selected from the group consisting of: nucleic acids; antibodies; peptides; polypeptides; carbohydrates; lipids; glycoproteins; lipoproteins; lipopeptides; lipopolysaccharides; small organic molecules and small inorganic molecules. When coated with an antigen or antibody, the particles are used in an "immuno-WGM" assay or "immuno-based WGM" assay.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occuring nucleotides with an analog (such as a morpholine ring), internucleotide modifications such as uncharged linkages (eg. methyl phosphonates, phosphotriesters, phosphoamidates, carbamates, etc.), charged linkages (eg. phosphorothioates, phosphorodithioates, etc.), pendent moieties (eg. polypeptides), intercalators (eg. acridine, psoralen, etc.), chelators, alkylators and modified linkages (eg. α-anomeric nucleic acids etc.). Also included are synthetic molecules that mimic polynucleotides in their ability to bind a designated sequence via hydrogen bonding and other chemical interactions. Such molecules are known in the art and include, for example, those in which peptide linkages substitute for phosphate linkages in the backbone of the molecule.

The term "antibody" refers to a protein of the immunoglobulin family that is capable of combining, interacting or otherwise associating with an antigen. An antibody is, therefore, an antigen-binding molecule. The term "antigen" is used herein in its broadest sense to refer to a substance that is capable of reacting with or binding to the antigen-binding site of an antibody. With reference to the present invention, an antigen also includes the idiotype of an antibody.

The term "immunoglobulin" is used herein to refer to a protein consisting of one or more polypeptides substantially encoded by immunoglobulin genes. The recognized immunoglobulin molecules include the κ, λ, α, γ ($IgG_1$, $IgG_2$, $IgG_3$, $IgG_4$), δ, ∈ and μ constant regions, light chains (κ and l), as well as the myriad immunoglobulin variable regions. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and $(Fab')_2$ and chimeric antibodies and all of these variants are encompassed by the term "antibody" as used herein. In addition, immunoglobulins from other animals (eg. birds, mammals, fish, amphibians, and reptiles) have similar function, but different nomenclature and these are considered "antibodies" as well.

In one embodiment, the analyte-binding ligand is a DNA molecule comprising a single-stranded DNA overhang, and the analyte to be detected is a nucleic acid molecule capable of hybridizing to the ligand. When hybridization occurs, a shift in WGM profile is detectable. Conversely, when there is no hybridization between complementary nucleic acid sequences, no shift in WGM profile occurs.

In a specific embodiment the analyte-binding partners or ligands are DNA molecules prepared by: (i) digestion of double-stranded DNA with an enzyme that generates a single-stranded DNA overhang, for example, a restriction endonuclease; and (ii) digestion with an exonuclease enzyme. The resultant digested DNA comprises single-stranded DNA capable of hybridizing to, inter alia, complementary single-stranded nucleic acids.

"Restriction endonuclease" as used herein means a nuclease enzyme that hydrolyses nucleotides at specific sequences within a DNA molecule. Restriction endonucleases comprise Type I, Type II and Type III restriction endonucleases.

Table 2 lists a subset of Type I and Type II restriction endonucleases that generate 5'-overhangs of 4 bases.

TABLE 2

Type I and Type II restriction endonucleases 5'-overhangs of 4 bases

| Enzyme | Overhang length | Sequence |
|---|---|---|
| BamHI | 4 | GATC |
| EcoRI | 4 | AATT |
| HinDIII | 4 | AGCT |
| AflII | 4 | TTAA |
| AgeI | 4 | CCGG |
| ApaLI | 4 | TGCA |
| ApoI | 4 | AATT |
| BanI | 4 | Variable |
| BclI | 4 | GATC |
| BglII | 4 | GATC |
| BsaI | 4 | Variable |
| BsaJI | 4 | Variable |
| BsaWI | 4 | GGCC |
| BseYI | 4 | CCAG |
| BsiWI | 4 | GTAC |
| BsmAI | 4 | Variable |
| BsmBI | 4 | Variable |
| BsmFI | 4 | Variable |
| BsoBI | 4 | Variable |
| BspEI | 4 | CCGG |
| BshHI | 4 | CATG |
| BspMI | 4 | Variable |
| BsrFI | 4 | CCGG |
| BsrGI | 4 | GTAC |
| BssHII | 4 | CGCG |
| BssKI | 4 | CCNG |
| BssSI | 4 | TCGT |
| BstEII | 4 | GTNA |
| BstYI | 4 | GATC |
| BtgI | 4 | Variable |
| DpnII | 4 | GATC |
| EaeI | 4 | GGCC |
| KasI | 4 | GCGC |
| MboI | 4 | GATC |
| MfeI | 4 | AATT |
| MluI | 4 | CGCG |
| NcoI | 4 | CATG |
| NgoMIV | 4 | CCGG |

TABLE 2-continued

Type I and Type II restriction endonucleases 5'-overhangs of 4 bases

| Enzyme | Overhang length | Sequence |
|---|---|---|
| NheI | 4 | CTAG |
| NotI | 4 | GGCC |
| PaeR7I | 4 | TCGA |
| PspGI | 4 | Variable |
| SalI | 4 | TCGA |
| Sau3AI | 4 | GATC |
| SexAI | 4 | Variable |
| SfcI | 4 | Variable |
| SgrAI | 4 | CCGG |
| SpeI | 4 | CTAG |
| StyI | 4 | Variable |
| TliI | 4 | TCGA |
| Tsp45I | 4 | Variable |
| Tsp509I | 4 | AATT |
| XbaI | 4 | CTAG |
| XhoI | 4 | TCGA |
| XmaI | 4 | CCGG |

Table 3 lists a subset of Type I and Type II restriction endonucleases that generate 3'-overhangs, mostly four bases in length.

TABLE 3

Type I and Type II restriction endonucleases 3'-overhangs, mostly 4 bases

| Enzyme | Overhang length | Sequence |
|---|---|---|
| AatII | 4 | ACGT |
| ApaI | 4 | CCGG |
| BanII | 4 | Variable |
| Bme1580I | 4 | Variable |
| BsiHKAI | 4 | Variable |
| Bsp1286I | 4 | Variable |
| BstXI | 4 | Variable |
| FseI | 4 | GGCC |
| HaeII | 4 | CGCG |
| Hpy99 | 4 | Variable |
| KpnI | 4 | GTAC |
| NlaIII | 4 | GTAC |
| NsiI | 4 | ACGT |
| NspI | 4 | GTAC |

TABLE 3-continued

Type I and Type II restriction endonucleases 3'-overhangs, mostly 4 bases

| Enzyme | Overhang length | Sequence |
|---|---|---|
| PstI | 4 | TGCA |
| SacI | 4 | TCGA |
| SphI | 4 | GTAC |
| TspRI | 8 | Variable |

"Exonuclease" as used herein means a nuclease enzyme that hydrolyzes nucleotides from the ends of DNA strands. One example of an exonuclease enzyme suitable for the preparation of the analyte-binding ligands and/or the analytes to be detected is lambda ($\lambda$) exonuclease. Lambda exonuclease is a double-stranded DNA exonuclease which degrades double-stranded DNA in a 5'- to 3'-direction. Lambda exonuclease requires the 5'-end of the DNA to be double-stranded and phosphorylated. Lambda exonuclease digestion can be used to preferentially degrade specific strands of double-stranded DNA to generate single-stranded DNA analyte-binding ligands and analytes to be detected.

In a specific embodiment, microspheroidal particles of the present invention are coated with nucleic acids derived from a pathogenic agent such as a virus, bacterium, yeast or parasite. The detection of a binding event is indicative of the presence of complementary nucleic acids in the sample and therefore, is indicative of the presence of the agent in the sample and/or at the source of the sample.

"Complementary" as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

The present invention is particularly useful for testing for the presence of a wide array of analytes in a single sample.

It is not necessary to know the identity of the analyte to be detected, nor is it necessary to label either the analyte or the ligand with, for example, a fluorescent or radioactive label.

Due to the sensitivity of the WGM detection means, the present invention is useful for the detection of rare analytes which are present in a sample at low concentrations. For example, in a specific embodiment, the invention is useful for the detection of trace elements or contaminants such as allergens, pyrogens and microbiological or chemical contaminants in foods and medicines; pollutants or toxicants in environmental and industrial samples; explosives; agents of bioterrorism; etc. As used herein the term "rare" means infrequently occurring or uncommon or relatively few in number or relatively low in concentration.

The present invention is also useful for the identification of analytes previously not known to bind to a particular ligand. For example, in a specific embodiment of the invention, the microspheroidal particles are coated with an enzyme or a receptor molecule in which the conformation of the catalytic site or putative ligand-binding site is intact. Analytes that bind to such particles represent putative agonists or antagonists of enzyme activity or receptor-ligand binding. In other words, the present invention is useful for drug identification and design.

Rational drug design permits the production of structural analogs of biologically active polypeptides of interest or of small molecules with which they interact (e.g. agonists, antagonists, inhibitors or enhancers) in order to fashion drugs which are, for example, more active or stable forms of the polypeptide, or which, e.g. enhance or interfere with the function of a polypeptide in vivo. See, e.g. Hodgson (*Bio/Technology* 9:19-21, 1991). In one approach, one first determines the three-dimensional structure of a protein of interest by x-ray crystallography, by computer modeling or most typically, by a combination of approaches. Useful information regarding the structure of a polypeptide may also be gained by modeling based on the structure of homologous proteins. An example of rational drug design is the development of HIV protease inhibitors (Erickson et al., *Science* 249:527-533, 1990). In addition, target molecules may be analyzed by an alanine scan (Wells, *Methods Enzymol.* 202:2699-2705, 1991). In this technique, an amino acid residue is replaced by Ala and its effect on the peptide's activity is determined. Each of the amino acid residues of the peptide is analyzed in this manner to determine the important regions of the peptide.

In another embodiment, the present invention is useful for the detection of genes or their encoded proteins associated with specific pathological conditions and diseases. For example, in a specific embodiment, the microspheroidal particles of the invention are coated with a specific ligand or library of ligands known to be expressed in human cancer, or conversely, with an antibody or library of antibodies specific for an antigen or antigens known to be associated with cancer. Therefore, the detection of a binding event is indicative of the presence in a sample of an analyte known to be associated with cancer. Due to its sensitivity, the WGM detection means of the present invention provides, inter alia, a method for the early detection of cancer.

In a further embodiment, the ligand or analyte to be detected comprises a single nucleotide polymorphism (SNP) or a specific post-translational modification.

The methods of the present invention are useful for several applications in the fields of, for example, medicine, veterinary science, agriculture, forensic science, biotechnology, food technology, sports science, nutritional science, manufacturing, drug design and development, biodefence, detection of explosive materials, insecticides, fertilisers and toxins.

Furthermore, the methods of the present invention are useful for diagnosis of pathological conditions or diseases including genetic diseases, cancer, autoimmune disorders, allergies, infectious diseases, heart disease, neurological disease, proteopathies, and metabolic diseases, virus and bacterial diseases and contamination, identification of unknown bacteria or viruses or other microorganisms in natural samples.

Still further, the methods of the present invention are useful for, inter alia, tissue typing, blood typing, genetic testing, drug testing, analysis of blood analytes, alcohol testing, pregnancy testing, etc.

The methods of the present invention are particularly useful for screening biological samples for the presence of an analyte. A "biological sample" is to be understood as a sample derived from a biological source such as an environmental sample, organism extract, plant or animal extract, serum, urine, exudate, semen, plasma, soil sample, river or sealed sample, extra-terrestrial sample, amongst other sources.

Another aspect of the present invention provides a biosensor. A "biosensor" as used herein means a sensor device for detecting quantities of, including very small quantities, or changes in a biochemical or chemical substance, in which an intermolecular binding event is registered and translated into data.

"Biosensing" as used herein means any of a variety of procedures which use biomolecular probes to measure the presence or concentration of biological molecules, biological structures, microorganisms, etc., by translating a biochemical interaction into a quantifiable physical signal.

The biosensing applications of the invention are in no way limited and include: environmental applications e.g. the detection of pesticides and river water contaminants; remote sensing of airborne bacteria or spores thereof e.g. in counter-bioterrorist activities; detection of pathogens; determining levels of toxic substances before and after bioremediation; detection of organophosphates; routine analytical measurement of biochemical analytes; detection of drug residues in food, such as antibiotics and growth promoters; drug discovery and evaluation of the biological activity of new compounds.

The present invention provides, inter alia, an optical biosensor based upon the WGM detection system. In a particular embodiment, the biosensor is compact and portable. The biosensors of the present invention provide a means for the rapid and sensitive detection of analytes.

In one embodiment, the biosensor is particularly adapted for convenient use in research and analytical laboratories and in the field. The WGM detection apparatus per se is adaptable to self-containment, miniaturization and portability. Importantly, this adaptability allows for rapid and convenient analyte detection on the bench-top or in the field, without any requirement for bulky and expensive components.

In a particular embodiment of the present invention, the WGM detection apparatus does not require a bulky power source or light source, nor an expensive spectrophotometer or optical lens. For example, some embodiments provide a 60× microscope objective lens and a non-chilled spectrophotometer is used with a 0.5 nm slit width. In some embodiments the WGM detection apparatus is a biosensor.

A power source of about 10 µW to about 2000 µW is sufficient to generate WGM spectral data according to the methods of the present invention.

In an embodiment, the fluorophore-conjugated microspheroidal particles of the present invention are exposed to light for about 20-2000 milliseconds. Light at a wavelength of 532 nM is particularly suitable for generating WGM spectra according to the present invention.

In certain aspects, the microspheroidal particles of the invention are immobilized by "baking" to a solid support matrix, e.g. glass. The solid support comprises material through which light in the infra-red, visible and ultra-violet spectra can travel.

In one embodiment, microspheres are dried to a glass surface for times greater than 10 minutes at temperatures above 40° C.

A key requirement of the system is that spectra can be automatically compared and differences between before and after binding can be quantified. This has been accomplished by using a log transformation of the time-mode spectrum.

The present invention also provides a kit for analyte detection by WGM means. Such kits comprise fluorophore-conjugated microspheroidal particles to which a multiplicity of analyte-binding ligands is attached. In an embodiment, the microspheroidal particles are immobilized to a glass surface. The multiplicity of ligands to be anchored to the microspheroidal particles can be designed to detect a specific array of analytes. For example, in a specific embodiment, an environmental sample is tested for the presence of one or more human pathogens of public health significance, e.g. *Legionella pneumophila, Mycobacterium tuberculosis*, vancomycin-resistant *Staphylococcus aureus* and the like. In one embodiment the microspheres are coated with a library of nucleic acids derived from a number of different pathogens. The combinations of ligands for anchoring to the microspheroidal particles is not limited.

When the microspheroidal particles are melamine formaldehyde, the kit may also contain quantum dots.

"Environmental sample" as used herein means a specimen of any material collected from an environmental source, such as air, water or soil. An "environmental source" as used herein relates to the natural environment, man-made environment or the extra-terrestrial environment. Other samples include food samples. Hence, the WGM assay is useful for the food industry, environmental water testing, the agricultural industry, bio-terrorism testing and pharmacological testing.

The particles may also be re-cycled for continual use and for high throughput screening.

The changes to the WGM indicate the presence of an analyte. It is also possible to glean further information from changes in the relative intensities, line widths and wavelengths of the WGM peaks of a particular microsphere.

The present invention is further described by the following non-limiting Examples.

EXAMPLE 1

Microspheroidal Particles (QSand-Trademark) Conjugated to a Multiplicity of DNA Ligands Demonstrate Consistent Shifts of WGM when Bound to an Analyte Fluorophore-conjugated microspheroidal particles (QSand [trademark: silica particles]) conjugated to a multiplicity of DNA ligands demonstrated a measurable and consistent difference after binding of specific analyte. Microspheroidal particles, either 4.87, 5.6, 6.8, or 7.5 μm in diameter were conjugated to a multiplicity of 22-mer DNA molecules with a TMR tag at nucleotide position 1. WGMs were acquired before and after hybridization with complementary 22-mer (FIG. 1).

EXAMPLE 2

Optimization of the WGM Apparatus for Biosensing

A number of parameters were assessed in order to determine whether the WGM detection system could be adapted for miniaturisation, self-containment and portability.

Figure 2:
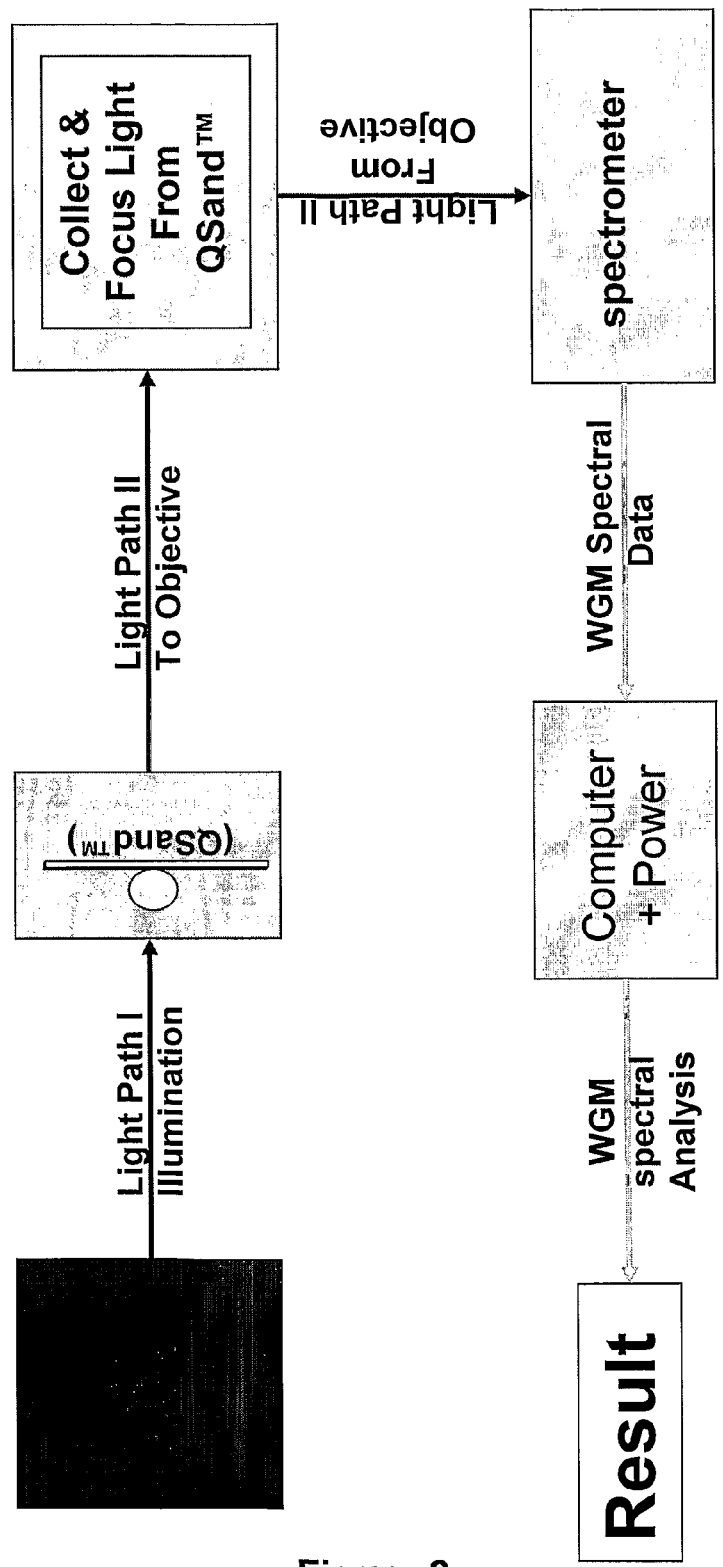
FIG. 2 is a schematic representation of the WGM detection means and apparatus.
Figure 3:
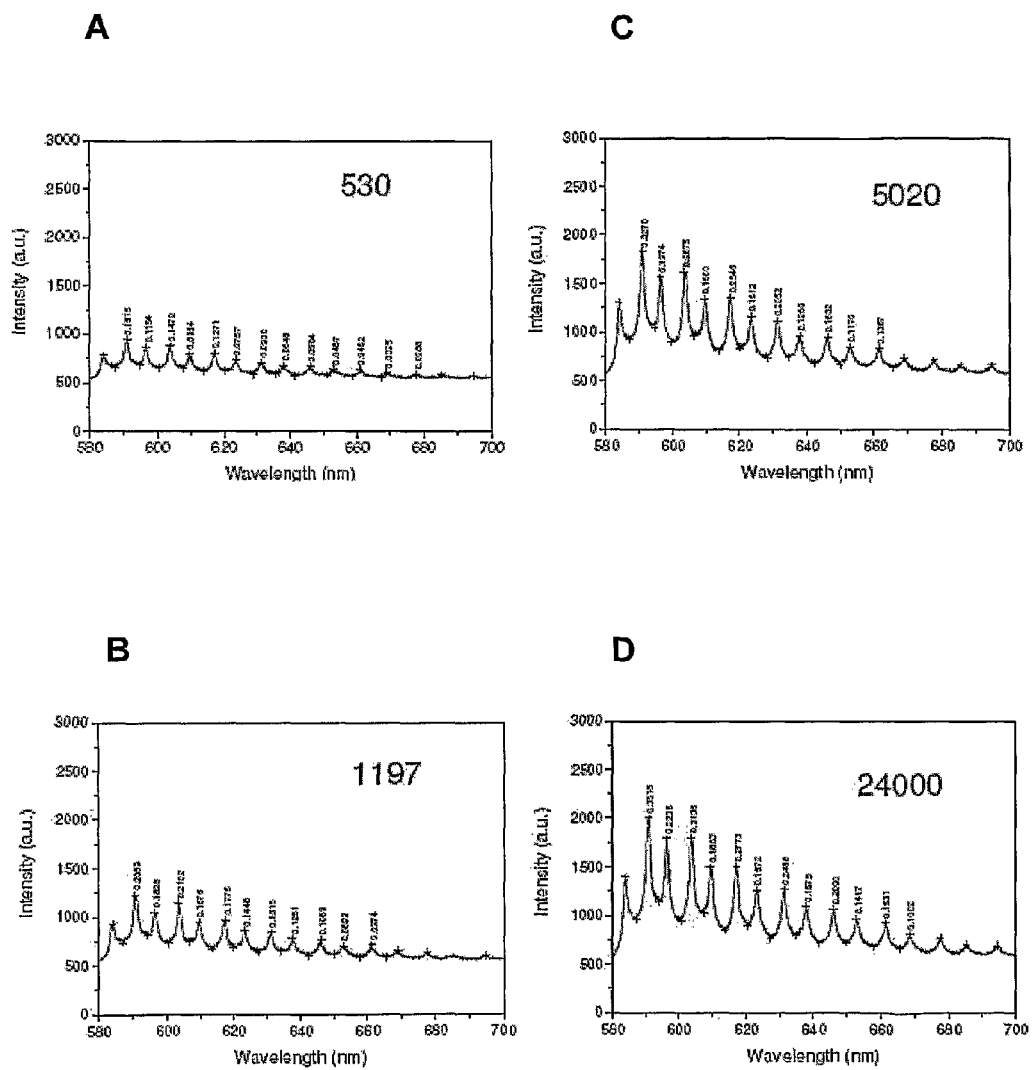
FIG. 3 is a graphical representation of WGM spectra generated with incident light of 6.3 μW, 50.2 μW, 214.5 μW and 1,160.5 μW (A, B, C and D respectively). The light source had a wavelength of 532 nm and the exposure time was 200 ms.

FIG. 2 provides a schematic illustration of the WGM detection system. First, the power of the light source was varied to determine its effect on WGM resolution. An incident power for the light source (532 nm, 200 milliseconds) of 6.3, 50.2, 214.5 or 1160.5 μW was sufficient to resolve WGMs (FIG. 3B). Such power is achievable with a standard low cost laser (light pointer).

The excitation time was varied in order to determine its effect on WGMs. WGMs were assessed following exposure for 10, 60, 200 and 1000 milliseconds of incident light (50 μW, 532 nm). It was determined that an exposure time as short as 200 ms was sufficient to resolve WGMs (FIG. 4C) with visibility decreasing up to 5 seconds exposure time (FIG. 4E).

200 milliseconds of exposure to 50 microwatt power light was shown to be adequate for high quality WGMs.

EXAMPLE 3

WGM Biosensor Prototype

The prototype WGM biosensor is built to specifications that result in well-resolved WGM spectra before and after binding of an analyte to a microspheroidal particle. The device is approximately 30×15×15 cm and 2-5 kg, and is completely self-contained comprising a power source, light source, sample handling chambers and spectrophotometer.

EXAMPLE 4

Microspheroidal Particle Immobilisation

Figure 5:
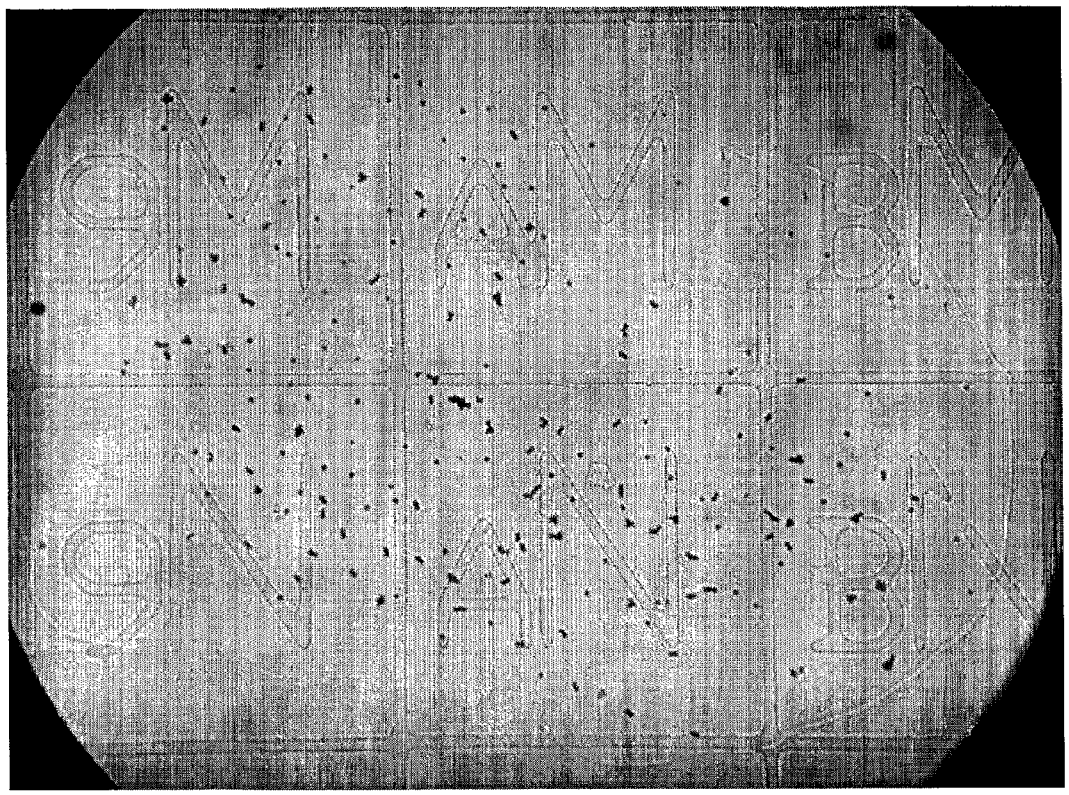
FIG. 5 is a photographic image of microspheroidal particles of the present invention immobilized on the surface of a glass coverslip.

Microspheroidal particles (QSand [trademark: silica particles]) were immobilized to the surface of a glass microscope slide coverslip in a random configuration (FIG. 5). The coverslip with immobilized QSand (trademark) particles was able to be coupled directly into the slit of the spectrometer.

EXAMPLE 5

Development and Characterization of a Single Particle Platform for Unlabeled Oligonucleotide Target Detection, Using Whispering Gallery Modes in Single, Fluorescent Microspheres In this Example, the development of an inexpensive, highly-sensitive, whispering gallery modes (WGM) based biosensing system is demonstrated. The system comprises a silica microsphere functionalized with a fluorophore and a dense monolayer of single-strand oligonucleotides. The adsorption of the complementary strand causes spectral shifts in the emission spectrum of the microsphere that can be registered using a conventional optical microscope and CCD detector.

Materials 7.50 μm $SiO_2$ microspheres were acquired from Micropar-ticles GmbH, Berlin, Germany. 5.06 μm and 6.80 μm silica particles were acquired from (Bangs Laboratories Inc, USA). Photoetched gridded coverslips (18×18 mm) were purchased from Bellco Glass, Vineland, N.J., USA. (3-mercaptopropyl) trimentoxysilane (MPS, 95%); tetraethyl orthosilicate (TEOS, 98%), polyvinylpyrrolidone (PVP, MW 40,000), Ammonium Hydroxide (29.1% wt % $NH_3$ in water); (2-[N-morpholinoethanesulfonic) hydrate (MES), sodium acetate (NaOAc), ammonium persulfate (>98%) and dimethyl sulfoxide (>99.9%) were obtained from Sigma-Aldrich. Analytical grade nitric acid, ethanol, methanol and 2-propanol were acquired from Merck, Victoria, Australia. Succinimidyl ester dye-label tetramethyl rhodamine (TMR), Bodipy 630/650 and Alexa 647 was purchased from Olecular Probes, Eugene, USA. Milli-Q grade (R>18 Ωcm) water was used throughout. Acryloyl modified oligonucleotides were designed in-house and constructed by Integrated DNA Technologies, Coralville, Iowa, USA. The oligonucleotide constructs were received dry and resuspended to 200 μM with ultra-purified Milli-Q H$_2$O before use.

Characterization Instrumentation

Ocean Optics Set-Up

Experiments were carried out on a Nikon Eclipse TE2000-S microscope. Excitation of the microsphere fluorescence was achieved with an 80 W Nikon mercury lamp through a 420-490 nm filter block. Whispering gallery mode emission signals from excited microspheres were captured in air with a QE6500 Ocean Optics spectrophotometer. All data were captured using the corresponding Spectra Suite software. Typically WGM spectra were collected within 1-2 seconds with a spectral resolution of ±0.9 nm with an 800 ms integration time. Excited light through the filter was measured to a consistent 35.52 mW radiation power. Particles were imaged through a Nikon Plan Fluor Oil immersion 100× objective, with a working distance of 1.30 mm. The spectral resolution (±0.9 nm) defines the accuracy with which a fluorescence peak wavelength can be measured. Peak shifts in a WGM response curve can be routinely observed between 0.1 nm up to several nm. The optical resolution stated by the manufacturer indicates peaks with 0.14 nm-7.7 nm FWHM can be routinely detected.

When utilizing the QE6500 peaks observed at 575 nm, 585 nm, 605 nm were generally used as reference peaks due to the low signal to noise and sharpness of individual peaks at these wavelengths.

Confocal Microscopy

In some cases a nitrogen cooled TRIAX 550 spectrometer (Horiba Jovin Yvon, USA) attached to an Lympus confocal microscope was used to collect spectra with a spectral resolution of ±0.05 nm. The results from both instruments were the same within experimental error. The TRIAX 500 spectromer which was increased sensitivity (calibrated spectral resolution ±0.05 nm) and scanning range (o-1500 nm) capabilities is utilized in combination with the Ocean Optics set-up to provide an effective platform to confirm and monitor WGM shifts particularly when detecting extremely low concentrated DNA samples.

Steady state emission spectra were recorded on a Jobin Yvon Fluorolog-3 Fluorimeter. A more extensive outline of the microscope set-up and scan conditions used is addressed in Example 6.

Scanning Electron Microscope (SEM)

Images of the microspheres were also collected using a Philips XL-30 field-emission SEM. To do this, microspheres were washed with Milli-Q H$_2$O and immobilized directly onto 12 mm circular silica substrates, which were then mounted onto SEM studs. The samples were sputter coated with 3-5 nm of gold using an Edwards 5150B Sputter Coater.

Oligonucleotide Fragment Design and Construction

The following single-stranded target and complementary oligonucleotide sequences were randomly designed and named for the sole purpose of this investigation; therefore homologies to known gene sequences are coincidental and should be disregarded. Designed sequences were synthesized and ordered from integrated DNA technologies, Coralville, Iowa, USA. The oligonucleotides were maintained as 200 μM working stocks in ultra-pure Milli-Q H$_2$O.

The oligonucleotide sequences and the shorthand names used throughout this Example are provided below. The modification "iAm" provides a free internal amine group (e.g. used to attach fluorophores) on the DNA fragment which essentially is a T nucleotide base with the free —NH group attached.

en1
(SEQ ID NO: 1)
(T)
5'-/Acrd//iAm/AT GGA ATT AAC CCT CAC TAA AGG GAG GAC AGC TAT GGA CTG CTT CTA CAC AGT CTC CTG TAC CTG GGC A-3'

α-en1
(SEQ ID NO: 2)
(T)
5'-CAG GAG AC/iAm/GTG TAG AAG CAG TCC ATA GCT-3'

40 base α-en1
(SEQ ID NO: 3)
(T)
5'-GT CCT CCC CTT CAG GAG AC/iAm/GTG TAG AAG CAG TCC ATA GCT-3'

20 base α-en1
(SEQ ID NO: 4)
(T)
5'-CAG GAG AC/iAm/GTG TAG AAG CAG-3'

10 base α-en1
(SEQ ID NO: 5)
(T)
5'-CAG GAG AC/iAm/G-3'

Control (random non-specific target sequence)
(SEQ ID NO: 6)
(T)
5'-/Acrd//iAm/TTA GGC CTA TGG ACA CGT GCG CAT GAT TTG CCT ATT CCG AAT CCG CAG GAT GGG CCT TAC A-3'

The sequence /Acrd/ denotes a 5'acryloyl group (Acrydite-trademark, Integrated DNA Technologies, USA) group attached to the oligonucleotide sequences and /iAm/ specifies the position of a modified T nucleotide base which possesses a free internal amine group used for fluorophore attachment (Integrated DNA Technologies, USA).

Methods

Microsphere Surface Functionalization

The silica microspheres used in this investigation were functionalized with thiol groups using standard literature procedures (Battersby et al, *Chemical Communications* 14:1435-1441, 2002; Corrie et al, *Langmuir* 22(6):2731-2737, 2006; Miller et al, *Chemical Communications* 38:4783-4785, 2005; Johnston et al, *Chemical Communications* 7:848-850, 2005; Verhaegh and Vanblaaderen, *Langmuir* 10 (5): 1427-1438, 1994). 5 mL aliquots of raw microspheres were washed in 20 mL of Milli-Q H$_2$O by centrifugation for 2 min at 1800 rpm. The pellet was resuspended in 20 mL of 1.5 M nitric acid followed by gentle inversion on a motorized stirring wheel for 30 min; the process was repeated three times. The microspheres were then washed with 20 mL aliquots of 2-propanol and refluxed in 2-propanol (20 mL) at 80° C. under constant stirring while (100 μL) 0.5% v/v of pure MPS was administered every 30 min over a 4 hr period to functionalize the particles with mercaptan groups. Functionalized spheres were washed at 1800 rpm with 2-propanol and resuspended in 10 mL of fresh 2-propanol. This microsphere slurry was divided into aliquots and pelleted at 8000 rpm for 5 s and dried in a desiccator under nitrogen for 230 min. Finally, they were agitated and heat cured to ensure complete 2-propanol evaporation (90° C.) for 30 min on a heating block. All functionalized microspheres were stored desiccated at 4° C. under nitrogen. The above procedure leads to reproducible, dense functionalization of the silica surface, and further ensures quantitative repeptization of the microspheres after storage.

Surface Layered Nanocrystal Doped Microsphere Synthesis

CdSe@ZnS nanocrystal core/shells were used which emitted orange with emission maximum 593 nm; FWHM 32 nm. Aliquots were taken from a 10 μM stock solution. MPS functionalized silica beads were combined with CdSe@ZnS core shell nonocrystals in a 1:2.5 ratio, manually shaken, then put onto a rotator at minimum rpm for 15 min-1 hr. Following passivation, 2-propanol was used to emulsify the two phases and the colloidal suspension was spun down at 800 rpm for 5 seconds; the supernatant was then discarded and several $CHCl_3$ washes were performed to remove free or non-adsorbed nanocrystals. 60 PVP molecules/$nm^2$ of surface area on the microsphere were required to coat the CdSe@Zns passivated microspheres, PVP was dissolved under stirring for 1 hr in 9:1 reaction solvent of $CHCl_3$: 2-propanol. The passivation pellet was resuspended in the reaction mixture and flash-vortexed and the reaction was allowed to react overnight. The polar amide group within the pyrrolidone ring on the PVP molecule most probably facilitates chemisorption to the nanocrystal surface via covalent bonds. In addition, due to the molecules amphiphilic characters, the coating offers stability to the microsphere (hydrophobicity and stability in water) and allows the molecule to be absorbed onto many surfaces. This increases the affinity of the particle to the final silica shell coating without the employment of a coupling agent. The following day reacted particles were washed several times (8000 rpm; 5 s) in 2-propanol and maintained 4° C. in 2-fresh propanol. The microspheres were capped in a 1:200 solution of TEOS, 1 mL of 4.2% (in $H_2O$) $NH_3$ solution was utilized per 1 mL of PVP capped particles in reaction and 1:200 TEOS volume (100 μL per 0.005 g of PVP capped microspheres). TEOS was added under stirring and allowed to react overnight followed by several washes in 2-propanol. All microspheres were kept suspended in 2-propanol and maintained at 4° C.

Oligonucleotide Base Specific Labeling

To dye-label the free-internal amine group of received 5' acryloyl enl and Control oligonucleotide sequences, 15 μL of 200 μM stock oligonucleotide was combined with 3.5 μL TMR succinimdyl ester-fluorophore and 4.5 μL of 1 M $NaHCO_3$ solution in an eppendorf tube. The solution was incubated in the dark (to minimize photo-bleaching of the dye) for 2 hr at room temperature with occasional mixing. To wash and precipitate the labeled oligonucleotides the preparation was treated with a mixture of 58 μL Milli-Q $H_2O$, 10 μL NaOAc, and 200 μL of ethanol, which were added directly to the reaction and the solution was then stored in a −20° C. freezer for 30 min. Samples were then centrifuged for 20 min at 13,800 rpm and the supernatant removed. These steps were repeated until the sample supernatant was free of excess fluorophore. Finally, the labeled oligonucleotides were diluted to a 200 μM working stock with 100 μL of ultra-pure Milli-Q $H_2O$ and stored in a −20° C. freezer.

Acryloyl Oligonucleotide Coupling to Microspheres

Figure 6:
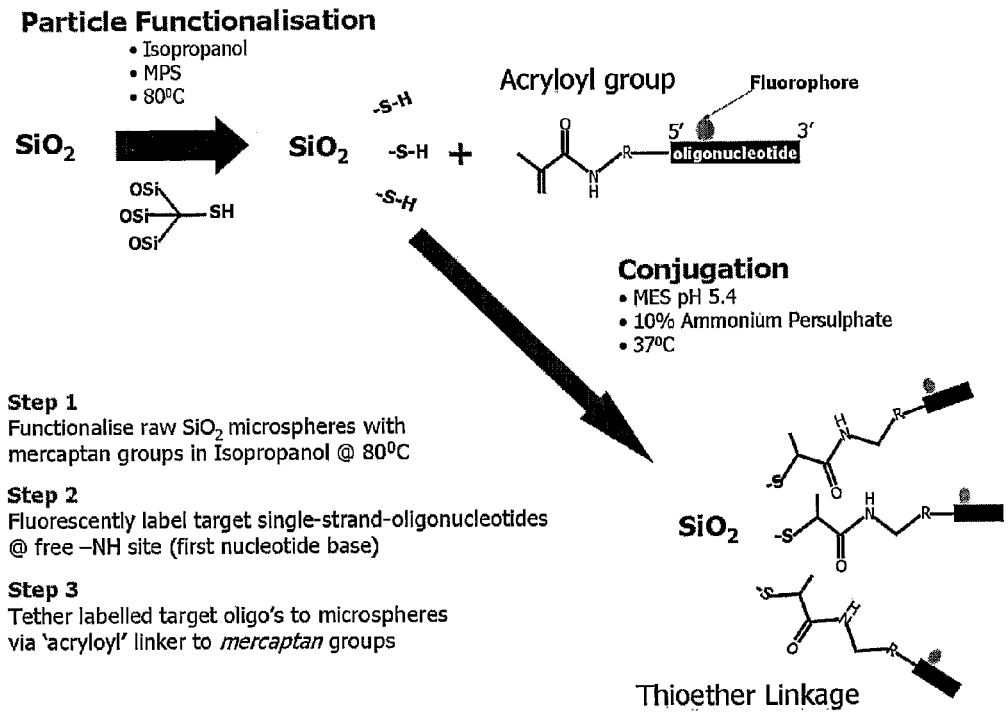
FIG. 6 is a photographic representation showing the simplified chemical reaction steps using a silica particle functionalized with mercaptan groups. Through covalent bonding the conjugation of fluorescently labeled acryloyl-single strand oligonucleotide fragments is achieved. This process leads to the robust cost effective fabrication of fluorescent microspheres which propagate WGM.

Thiol functionalized microspheres were derivatized with enl and Control target 5' acryloyl modified oligonucleotides using standard protocols (Hermanson, *Bioconjugative Techniques*, Sand Diego: Academic Press Incorporated, 785, 1996) as follows: In an eppendorf tube 0.002 g of functionalized MPS microspheres were weighted out and then saturated with 100 μL of methanol via microcentrifugation (8000 rpm for 5 s), and the supernatant discarded. The pellet was resuspended in fresh 0.5 M MES (pH 5.4), followed by the addition of 15 μL of 200 μM acryloyl-modified TMR-labeled oligo-sequence (enl or Control) along with 100 μL fresh 10% w/v ammonium persulfate (w/v). The reaction was vortexed and then gently mixed on a motorized wheel for 1 hour. The coupled microspheres were washed with Phosphate Buffer Saline (Buffer) [ph 9.0] and pelleted in a microcentrifuge (8000 rpm for 5 s) to remove the supernatant. All oligo-conjugated microsphere preparations were resuspended in 1 mL buffer (2 g of spheres/liter) and stored at 4° C. The methods utilized to routinely fabricate fluorescent oligonucleotide modified silica particles which produce WGM presented in this Example and later presented in Example 6 are illustrated in FIG. 6. These particles are utilized to demonstrate the robust and highly sensitive detection capabilities of WGM when utilized in a DNA specific recognition platform.

Method for Microsphere Immobilization to Gridded Array Plate

For each assay plate, 10 μL aliquots (20 μg of microspheres per assay) of enl or Control microspheres were washed 3-4 times separately in eppendorf tubes with 1 mL portions of Milli-Q $H_2O$ (8000 rpm for 5 s). The washed microspheres were resuspended in 120 μL of Milli-Q $H_2O$ and vortexed and spotted onto individual gridded silica plates. Each particle-mounted array was then placed on a heating block/plate (90° C.) to immobilize the particles and completely evaporate off any excess water. During heating the array plates were gently vortexed by coupling a vortex mixer to the heating block to ensure thorough dispersion of the colloids.

Hybridization Cycle Conditions

As in polymerase chain reaction (PCR) preparations (Rychlik et al, *Nucl. Acids Res.* 18(21):6409-6412, 1990) a two-step temperature gradient was employed for all hybridization reaction cycles. Once cDNA had been administered, the array plate was placed on a 90° C. heating block for times ranged from 10 s-5 min. Thereafter, the arrays were cooled to room temperature over 5 min to ensure sufficient time for cDNA probes to anneal onto target oligonucleotides.

Single Particle cDNA Hybridization Assay

A sample of 200 μM stock cDNA solution was diluted with PBS (1:40), and the sample was vortexed. A 120 μL, aliquot was applied to each array plate (enough to completely immerse the gridded array area). Each particle-mounted array then underwent 90 s single hybridization cycle. For the control-reagent assay each grid was treated with 120 μL of the control solutions: Milli-Q $H_2O$ followed by buffer (PBS), non-specific DNA and cDNA (as above) and a hybridization cycle of 90 s was run for each treatment plate. All arrays were allowed to stand at RT for 5 min then gently washed with 100 μL portions of Milli-Q $H_2O$ to remove any solution phase (unreacted) DNA. Unless otherwise noted, excess water in all assays post cDNA treatment was removed by evaporation on a heating block (90° C.). The fluorescence excitation and emission signal measurements from treated spheres were then captured in air.

cDNA Denaturation Assay

Hybridization was carried out as above and then denaturation was effected by heating the hybridized samples on a 90° C. heating block for 30 s. The buffer was immediately removed by several 100 μL washes with Milli-Q $H_2O$. The denaturation steps were repeated three times, followed by the evaporation of excess liquid and finally the measurement of emission from selected particles.

Particle Characterization Study

Particle Fabrication

The initial goal of this Example involved the surface functionalization of silica microspheres (<10 μm) with CdSe core shells (emitter) to enable a WGM signal to be created via ultraviolet (UV) illumination (Gomez et al, *Small* 1(2):238-241, 2005). The NC particles were then capped with several organic stabilizing layers and the final functional layer was intended to be with a selected bio-molecule. Unfortunately, the stability of the nanocrystals utilized in the experiments was compromised; progressive treatments led to consistent photodegradation and a loss of discernable WGM peaks before any possible conjugation with a biological molecule could be performed. The significant loss of photoluminescence was probably due to the desorption/break down of the nanocrystal layer. The photo-stability of the nanocrystals was clearly compromised when exposed to the reaction solvents utilized in the PVP and TEOS capping phases. The next investigation profiles the alternative approach, which involved the surface functionalization of a microsphere with dye-labeled, single-strand, oligomeric fragments directly to a thiol functionalized particle surface. The alternative approach forms the basis of the subsequent Examples.

Single Particle Hybridization Assay

Every single functionalized microsphere exhibits a unique WGM fingerprint. Consequently, it is necessary for bioassays to be carried out on the same particles before and after exposure to a test solution. To achieve this, the particles were immobilized onto a gridded-silica array and a detailed microsphere map of the en1-target and Control assay grids was collected. Each microsphere was numbered according to the other of its emission signal being measured; its specific location was then mapped out using the corresponding scannumber which was noted on a graphical schematic that represented a single etched grid. Using the gridded arrays, the same microsphere could be routinely re-located after exposure to various test solutions and controls. However, the refractive index of the microspheres is quite low and it was difficult to obtain high-quality WGM spectra from microspheres immersed in solution due to the low refractive index contrast. This was a fundamental problem and unexpected. The refractive index mismatch between colloidal silica and water is insufficient to support a WGM. Consequently, the protocols were designed so that all spectra could be collected in air.

The array plates were treated with a 120 µL does of the target complement α-en1. The initial hybridization step involved the assay grids being placed on a 90° C. heating block; by slowly heating the solution, any oligomeric or aggregated DNA that is present in the target solution is peptized to facilitate hybridization with the probe DNA on the bead. The acryloyl/sulfhydryl bond formed when probe oligonucleotide was conjugated to the microspheres surface effectively tethered and immobilized the target-probe sequence to the spheres surface and was not effected by subsequent heating 90° C. The arrays were cooled for 5 min at RT to allow sufficient time for the α-en1 cDNA probes to anneal to en1 target microspheres. The grids were then washed and all excess water was removed by evaporation on a heater block. Following treatment with the α-en1 probe the same individual particles were relocated and a second set of spectra were collected in air. A fluorescence spectrum of the dye-label TMR employed to label en1 and control oligonucleotide target sequences was fluorometrically analyzed. The emission range of the dye demonstrated the expected range of the microsphere emission signal which should be defined by the emission range of the selected fluorophore. The WGM emission signal falls within the excitation range of the TMR dye. The WGM spectra show a clear red-shift, though not every peak shifts equally. For the sample shown, the peak displacements observed post cDNA α-en1 hybridization measured at wavelengths 575 (1.1 nm), 585 (1.5 nm), 595 (1.1 nm) and 605 nm (1.1 nm) are all to longer wavelengths compared to the pre-hybridization emission signal, i.e. hybridization lead to red-shifts of the major peaks in the WGM spectrum.

Non-Specific Binding, Control Reagents and Buffer Effects

A control assay was then established to investigate the effects of control reagents on gallery mode signal. A single assay plate was treated with Milli-Q $H_2O$, a non-specific DNA sequence and finally the cDNA probe. A 90 s hybridization cycle was run for each stage treatment, the selected spheres were relocated and the fluorescence spectra collected after each stage. When the selected microsphere was exposed to Milli-Q and non-specific DNA treatment there was no consistent peak shift observed. However consistent red-shifts were observed when the microsphere was exposed to cDNA (α-en1). The cause of the resulting blue-shifts is unclear following Milli-Q $H_2O$ treatment however in comparison to exposure to the complementary target DNA, the key result is that there is no relationship noted post non-specific DNA and control reagent treatment. This is not a signal to noise concern as the single-particle format of the experiment accommodates for this so at this stage the result simply suggests the blue-shift is a random non-specific result.

Cycling of the WGM Assay

The aspect involved testing whether the assays are reversible, that is, whether denaturation of the DNA would result in a blue-shift to the original position and whether the hybridization reaction carried out a second time on the same microsphere would also cause a red-shift. This would enable us to confirm that the spectral shifts are due to biomolecular recognition and not just non-specific binding by DNA. Furthermore, the ability to cycle through repeated adsorption-desorption cycles would enable a more statistically reliable assay to be designed, in which the peak shifts over several cycles could be averaged. After hybridizing the cDNA to the probe microsphere, it was annealed at 90° C. in dilute buffer to try and denature the DNA and cause desorption of the target sequence.

Figure 7:
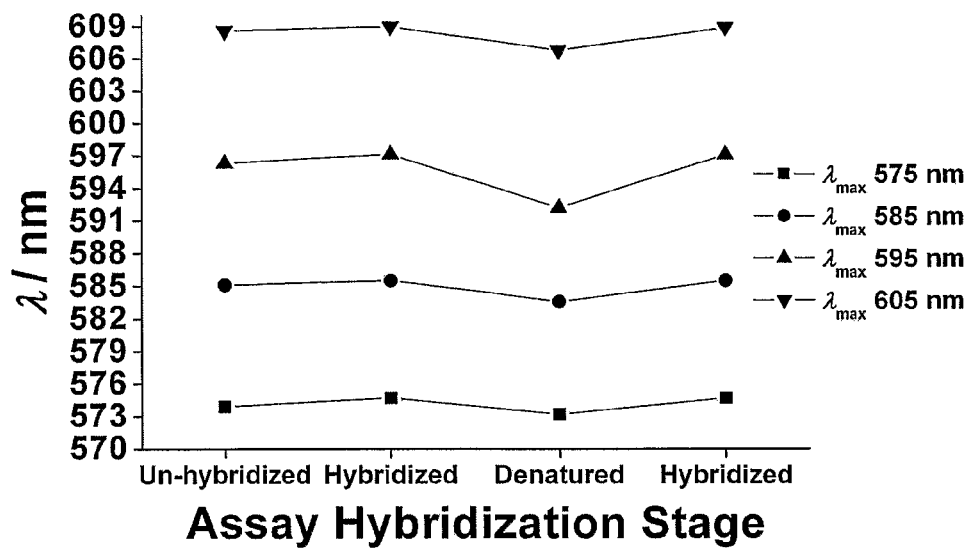
FIG. 7 is a graphical representation showing the plot of the peak positions of four major WGM peaks from a single microsphere as a function of the assay stage at which they were recorded. The plot clearly demonstrates the four major peaks red shift during hybridization, blue shift during denaturing and red shift again upon re-exposure to the target.

The spectra were recorded and the shifts are shown in FIG. 7, together with results of a second hybridization cycle. As can be seen, extended annealing in diluted buffer does lead to a blue-shift of all four major peaks, and a second hybridization does result in a red-shift, indicating that the assay cycles can be repeated, though the observed shifts are not consistent with complete reversibility. FIG. 7 is a simplified representation of the peak positions at each stage of the hybridization assay from a selected relocated sphere.

EXAMPLE 6

Attomole Detection of Label-Free Oligomeric Targets Using Whispering Gallery Mode in Single Fluorescent Microspheres In this Example, the sensitivity and limit and the speed with which the assay can be performed is determined.

Example 5 showed that single silica colloids functionalized with single-strand oligonucleotide fragments and can delineate between differences of 10 nucleotide bases of a cDNA target probe. In this Example, the results demonstrate that the WGM based system is capable of rapid, target-specific detection of complementary DNA fragments at room temperature (RT), at sub-picomolar concentrations and within just a few minutes using samples of several microliters. The results indicate that attomole detection of unlabeled DNA fragments is possible on a routine basis.

Experimental Section

Figure 8:
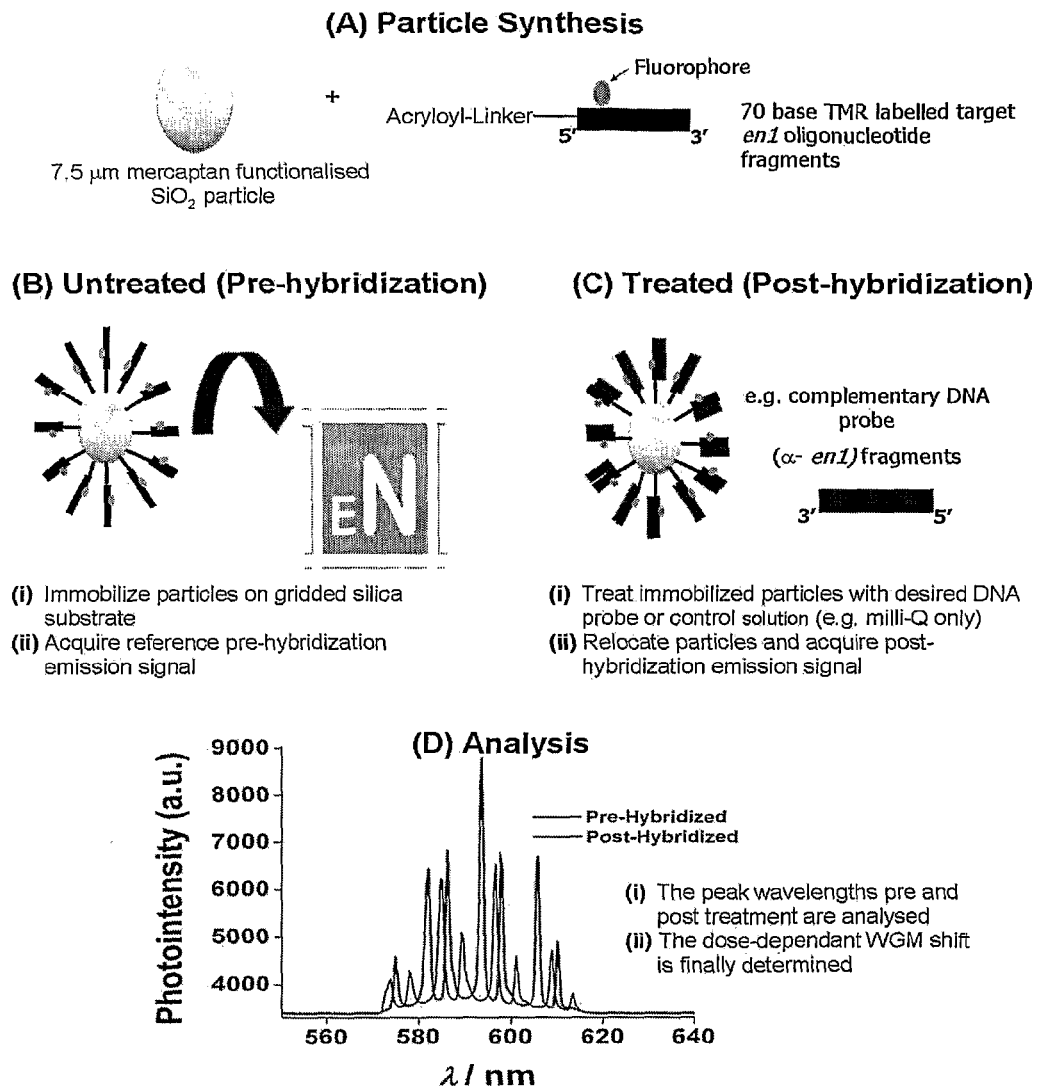
FIG. 8 is a photographic representation showing an overview of particle synthesis and WGM hybridization assay. Part A) indicates the key features of the 70 base en1 oligonucleotide-modified 7.50 μm $SiO_2$ microspheres. TMR=dye-label tetramethyl rhodamine; Part B) Particle assay plate preparation particles are immobilized on the hybridization substrate which follows the acquisition of emission signal (pre-treatment); Part C) Assay plates are treated with a DNA probe or control solution, followed by substrate washing and finally emission signal acquisition; Part D) The final step involves the analysis of the pre/post-emission signals from a single particle, the peak positions from the acquired spectra are compared to determine the effect of the treatment solution.

A simplified schematic which details particle synthesis and hybridization assay methods are outlined below (FIG. 8). The DNA fragments utilized were as used in Example 5 along with the whispering gallery mode characterization apparatus.

Instrumentation and Characterization Methods

Higher resolution spectra were collected in air on a FV-500 Olympus Fluoview laser Scanning Microscope IX71 (Olympus, USA) coupled to Triax 550 spectrometer and a CCD-3000v external detector (Jobin Yvon, USA). Particles were imaged through an Olympus UPlanSApo Oil immersion 100XO objective, with a working distance of 0.13 mm. Spectra could be collected within 5 s-2 min (depending on wavelength scanning range) with a spectral resolution of 0.05 nm. Sample photoluminescence and spectra were collected using a liquid nitrogen cooled (137 K) CCD camera. Particles were excited through a Melles Griot X2 multi-line Ar+ laser (Melles Griot, USA) typically at an excitation power of 350 µW. Emission signals were typically collected with the wavelength centre point at 600 nm through a 550 nm cut-off filter with a 2 s integration time.

Methods

A 'real' assay environment is one in which functionalized particles are exposed to various control reagents, specific and non-specific unlabeled analyte and hybridization buffers under various reaction conditions as prescribed in Example 5. A competitive detection platform in the current market should be able to routinely detect sub-picomolar concentrations of analyte. This Example investigates whether the WGM assay can be performed at room temperature and the detection limit of the system presented in Example 5 is determined. Unless otherwise stated, the assays performed in this Example were as prescribed in Example 5.

Sensitivity Complementary Probe Hybridization Assay

For the following hybridization assay serial dilutions were performed with the 200 µM stock α-en1 cDNA solution to create target solutions ranging in cDNA concentration from $10^{-15}$ M to $10^{-7}$ M. Each sample was thoroughly vortexed and a 120 µL aliquot of each probe solution was applied to individual en1 target arrays. Each particle-mounted array was then placed on a 90° C. heating block and the hybridization reaction was run for 90 s. The samples were allowed to stand at room temperature for 5 min and gently washed with 100 µL portions of Milli-Q H$_2$O. Post-treatment the array-plates were washed with Milli-Q H$_2$O to dilute the saline reaction buffer, and ensure that when excess reactant was evaporated off that salt-crystal deposition on the assay plate was minimized. Particles were then recovered and the relevant 'post-hybridization' emission signals measured.

Room Temperature Hybridization Kinetics Assay

Five arrays were prepared with immobilized en1-target sensors. The corresponding particle maps were noted and the WGM spectra were collected through fluorescence microscopy and excitation as detailed above. Given the assay was performed at RT, the probe treatment prepared in buffer ($2.50 \times 10^{-8}$ M α-en1) was heated for 10 min at 90° C. prior to use to ensure α-en1 DNA fragments were single-stranded. Each prepared array-plate was then treated with 120 µL aliquots of the single-stranded $2.50 \times 10^{-8}$ M α-en1 solution made in buffer. The arrays were then run for a single hybridization cycle of either 10 s, 30 s, 60 s, 180 s or 300 s at RT. Post-treatment array-plates were allowed to stand for 5 min at RT, washed with Milli-Q H$_2$O and dried. Sensors were then recovered and the relevant emission signals measured.

Sensitivity and Room Temperature Hybridization Investigation

Single Particle WGM Assay

Gallery mode signatures were acquired from 7.50 µm silica particles functionalized with TMR labeled 70 base-oligonucleotide fragments using two characterization set ups. The first a TE2000-S Nikon fluorescence microscope coupled to an ocean optics CCD (±0.9 nm) detector (FIG. 8A) and higher resolution spectra were acquired using an Olympus Fluoview laser Scanning Microscope IX71 (Olympus, USA) coupled to a TRIAX spectrometer (±0.05 nm) FIG. 8B. The key feature of the developed recognition platform is the 'single-particle' method utilized for particle scoring. The following schematic (FIG. 8C) illustrates the fundamental reason for the chosen format and why it is crucial in a WGM based system. The key point to take from the schematic is that to use the optical properties of WGM in a detection platform, averaging spectra from ensemble results can not be performed successfully as the example shows two identically modified particles, from the same sample have unique emission signatures. Ultimately, a single particle acts as its 'own-reference', thus a single particle can be seen as a single experiment. This parameter formed the fundamental analytical variable in the developed hybridization assay.

Sensitivity

Figure 9:
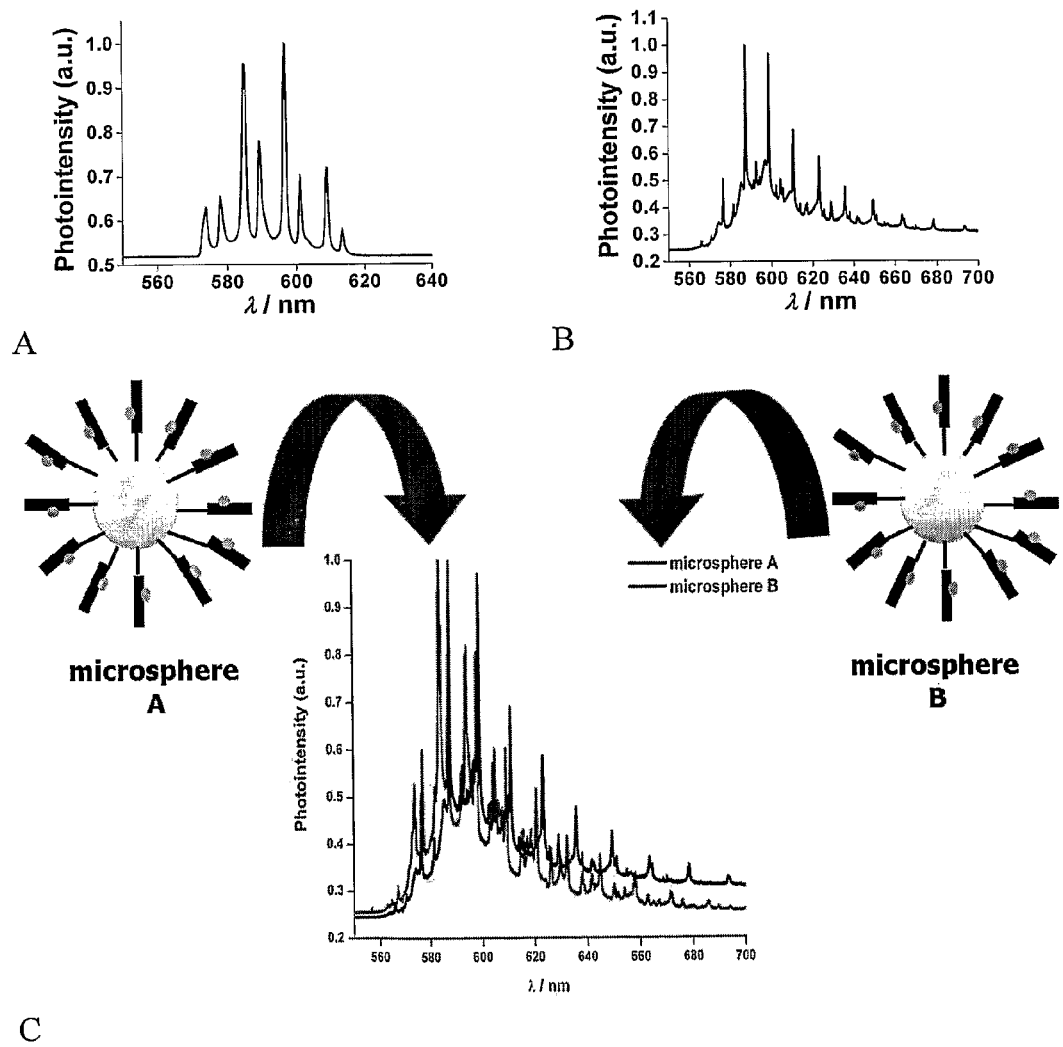
FIG. 9 is a photographic representation showing typical WGM emission signal outputs and single particle spectroscopy. A typical emission signal captured in air from an excited 7.50 μm oligo-modified silica particle using two WGM characterization set-ups A) Coupled to an Ocean Optics spectrometer (±0.9 nm) and B) Triax spectrometer (±0.05 nm); C) The concept of single particle spectroscopy, the schematic shows two particles, labeled microsphere A and B each from the same sample, both particles have been identically chemically modified. Note the emission signals acquired from the individual particles are distinctly unique.

An initial serial dilution (buffer) of the cDNA probe stock was prepared with concentrations ranging from $10^{-7}$ M to $10^{-15}$ M. The emission signals from a selection of individual microspheres were captured pre- and post-cDNA treatment exposure. The emission peak wavelengths or mode positions at the wavelengths close to 575, 585, 595 and 605 nm were analyzed as a function of the cDNA concentration (FIG. 9A). FIG. 9B presents the relationship between the peak shift ($\Delta\lambda$) of the emission spectra as a function of the cDNA concentration. There is a clear red-shift in the emission spectra after exposure for virtually all the WGM emission peaks in contrast to the (Milli-Q treatment) control assay which resulted in no consistent directional peak displacement. For assay purposes, it is sufficient to point out that virtually all the modes exhibit a red-shift upon adsorption of the DNA. Furthermore, it is reversible upon denaturation of the DNA at temperatures above the melting temperature. Given that the $\Delta\lambda$, shifts were just 1-4 nm for most assays, a more detailed investigation of the mode shifts was carried out using a Triax 550 spectrometer with ±0.05 nm spectral resolution. FIG. 9C presents a typical WGM spectrum from the same en1 target particle before and after cDNA exposure.

It is important to recognize that since each individual microsphere has its own WGM signature, detection is based solely upon the shifts observed or not observed with the same individual microsphere. Averaging of the results over multiple microspheres is not possible. At the present time, the actual shifts observed for positive detection with any individual microsphere are typically 1-2 nm for the microspheres employed and less than this for controls. Thus whilst the detection levels are extremely low, each experiment can only be correlated to the behaviour of the same particle. Data such as that shown in FIG. 9A, where the results from different microspheres are shown, the differences in the absolute shifts for each particle are not meaningful. The criteria for detection are whether consistent spectral shifts are detected by any single particle for a given exposure to reagents.

Discussion

The spectral resolution of the CCD set-up generally employed in this investigation could limit the sensitivity of the WGM sensors. The sensitivity depends critically on the spectral resolution of the detector employed. The Ocean Optics detector has a resolution of 0.9 nm, and the WGM emission peaks are damped due to the low spectral resolution. Hence, there is no information that can be gleaned from the mode shapes. Nevertheless, these simple spectrometers enable the assay to be carried out cheaply and could be done in the field routinely.

Hybridization induced red-shifts are routinely observed with 70 base-oligo-modified particles treated with sub-picomolar cDNA concentrations from a 120 µL dosage volume. Benchtop, LN2-cooled CCDs and grating monochromators are necessary to properly observe and characterize the WGM modes of the microspheres, but for assay purposes such high resolution is not a pre-requisite. At the lowest DNA concentrations, one can observe small, random blue-shifts from post hybridized particles. These indicate that the WGM emission can be influenced by small perturbations such as minute changes in the solution refractive index due to temperature fluctuations and electrolyte concentration. This determines the ultimate practical limit in sensitivity possible for these bioassays in aqueous media. Consequently, only consistent red-shifts of four or more peaks are taken to indicate a positive detection event.

It has also been demonstrated here that the system can be successfully employed at room temperature with target detection indicated by resonance mode shifts in microsphere emission signals within 10 seconds of cDNA exposure. This minimizes the problems associated with salt deposition and crystallization, pH changes, drying and contamination that occur when the microsphere environment is temperature ramped to denature any non-specifically bound probe and enable effective annealing of the DNA to the microspheres. The improvements mentioned above are important for the overall development of WGM based bio-detection platform for DNA analysis.

EXAMPLE 7

Solution Based Label-Free Detection of Single Nucleotide Polymorphism Targets, Using Whispering Gallery Modes in Single, Melamine Microspheres A disadvantage of silica-based WGM platform is it cannot be used entirely in solution. In this Example, the limitations associated with the current WGM system are alleviated by designing a conjugation protocol along with the development of a highly-sensitive, whispering gallery mode (WGM) solution based genotyping system. The system comprises a uniform, highly-cross linked melamine formaldehyde microsphere (≅7.52 µm) functionalized with a fluorophore and a monolayer of single-strand oligonucleotides. Using a microplate-well system an assay can be completed entirely in solution. The WGM label-free system can score polymorphic amplified DNA targets at sub-picomolar sensitivity. The frequency shifts detected in water can be used to monitor the denaturation of the double-stranded post-hybridization complex at elevated temperatures. Controlled by a two-step temperature gradient the optical switching capability of the polymer based sensor is also demonstrated as the WGM shifts can be reversed and re-activated routinely.

With this in mind biocompatible melamine composite particles are commercially available in a wide range of particle sizes (300 nm-12 µm). The material's high refractive index ($n_r$ 1.68) which is greater than that of polymethylmethacrylate ($n_r$ 1.48), silica and most other glass materials ($n_r$ 1.47-1.50) offers a clear advantage. Calculations using Mie theory suggest, the increased refractive index mismatch between an MF particle and an external water-medium ($n_r$ 1.33) should improve the quality factor of the WGMs. Importantly, the mismatch is large enough that it enables simplified assays to be carried out in solution.

This Example examines the development of a single particle, label-free WGM 'wet-assay' for oligomeric target detection. The particles possess Q factors similar to those of silica microspheres of the same size in air. Using the luminescent WGM signals the assay can routinely detect sub-picomolar levels of unlabeled oligonucleotide fragments in solution in a micro-well plate bench-top format. The findings presented show that fluorescent WGM signals in highly cross-linked melamine formaldehyde (MF) microspheres (<10 µm) positively discriminate a single nucleotide polymorphism (SNP) between unlabeled PCR amplified fragments of genomic DNA (gDNA) of three individuals carrying a different nucleotide at a particular loci.

Experimental Section

Materials 7.52 µm Melamine Formaldehyde Resin ($C_5H_8N_6O$). [MF] microspheres were acquired from Microparticles GmbH, Berlin, Germany. 384 well polycarbonate micro-titre plates, 96 well cell culture plates and 384 well optical micro-titre plates were purchased from NUNC, Brussels, Belgium. Succinimidyl ester dye-label Bodipy 630/650 were sourced from Molecular Probes Eugene, USA. All other reagents, buffers and composite microspheres were sourced from previously reported suppliers. All instrumentation and WGM characterization methods utilized are as described in Examples 5 and 6.

Instrumentation

A microscope PE100-NI system inverted peltier stage was utilized for thermocycling hybridization studies. The system comprised a diaphot range of inverted scopes with XY table customized for a Nikon TE200/300 microscope table. The stage temperature range (−5 to 99° C.) was controlled with a PE100-I heating/cooling peltier stage. The stage was coupled to a water circulation pump to regulate stage temperature. With minor modifications the above set-up was also mounted onto a IX71 Olympus microscope.

```
Human SNP target DNA sequences
rs10434 Target (conjugated to particle)
                                          (SEQ ID NO: 7)
             (T)
5'-/5Acrd//iAm/TC GCC GGG ACA TCT GCC AGT GG[T]

CTC CTG-3'

α-rs10434 A (complement)
                                          (SEQ ID NO: 8)
                    (T)
5'-CAG GAG [A]CC AC/iAm/GGC AGA TGT CCC GGC

GAA-3'

α-rs10434 B (mismatch)
                                          (SEQ ID NO: 9)
                    (T)
5'-CAG GAG [C]CC AC/iAm/GGC AGA TGT CCC GGC

GAA-3'

* Brackets denote the nucleotide base mismatch
```

The DNA fragments listed above were labeled as prescribed in Example 5 unless stated otherwise (Nuhiji and Mulvaney, *Small* 3(8):1408-1414, 2007).

rs10434 SNP region.

(SEQ ID NO: 10)
5'-TGG AAG ATT CAG GAG CCT GGG CGG CCT TCG CTT ACT

CTC ACC TGC TTC TGA GTT GCC CAG GAG [A/G] CC ACT

GGC AGA TGT CCC GGC GAA GAG AAG AGA CA-3'

PCR amplified regions of gDNA containing the rs10434 SNP labeled Individual 1 [A/A]; Individual 2 [A/G]; Individual 3 [G/G] were provided by the International Diabetes Institute (Melbourne, Australia). Genotyping was carried out using the MassARRAY system (Sequenom, San Diego, Calif.), as previously described (Peyrefitte et al, *Mechanisms of Development* 104(1-2):99-104, 2001). Briefly, PCR primers were designed for rs10434 using SpectroDESIGNER to amplify a 97 bp fragment surrounding the variant site. Reactions were performed using 2.5 ng genomic DNA, 2.5 mmol/L $MgCl_2$, standard concentrations of other PCR reagents and 0.1 unit HotStar Taq DNA polymerase (Qiagen, Germany) in a total reaction volume of 5 µL. Fragments were isolated by electrophoresis using Qiaquick gel extraction kit (Qiagen, Germany) as per the manufacturer's instructions.

Forward Primer
****ACGTTGGATGATGTGTCTCTTCTCTTCGCC (SEQ ID NO: 11)

Reverse Primer
****ACGTTGGATGCCTTCGCTTACTCTCACCTG (SEQ ID NO: 12)

Figure 10:
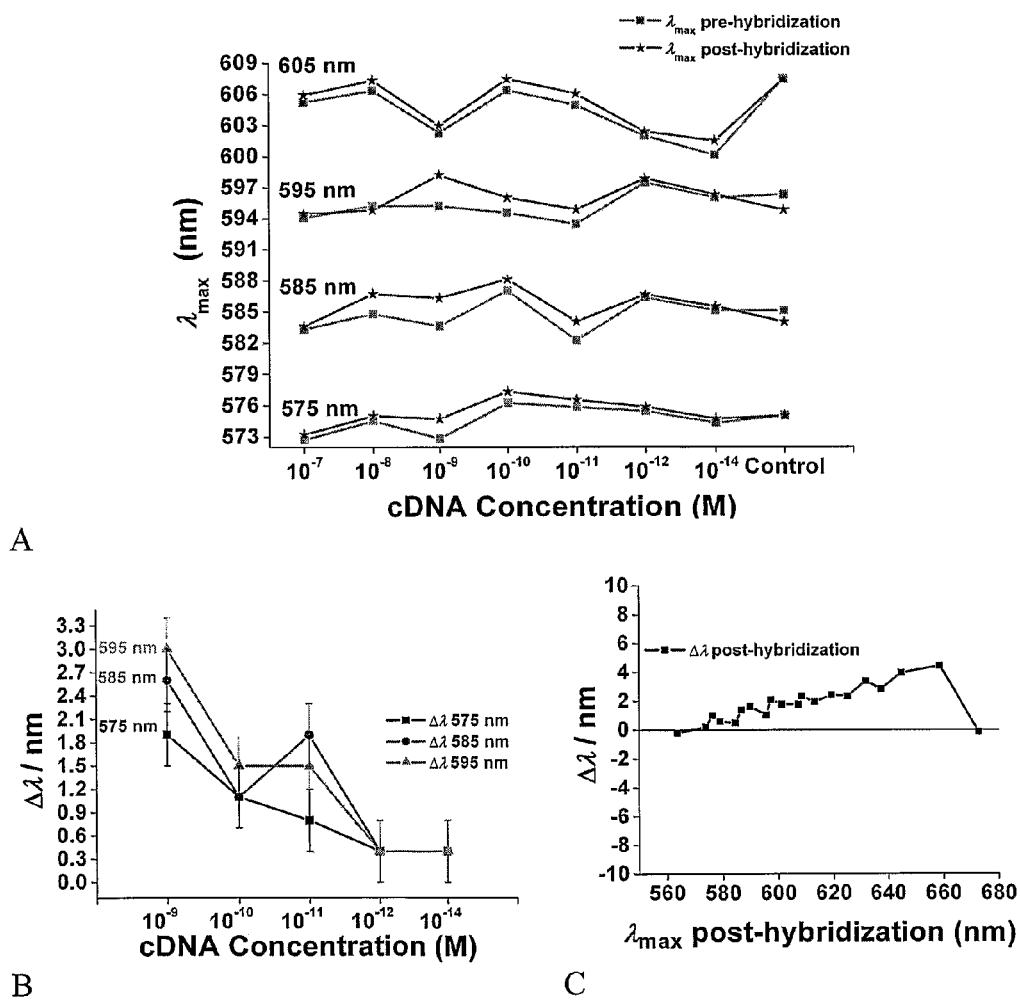
FIG. 10 is a graphical representation showing single microsphere spectral shift data from a selection of sensors used in a concentration based cDNA hybridization assay. A) The peak-positions plotted pre-(green-line solid boxes) and post-hybridization (red-line solid stars) against the cDNA concentration referred at four reference wavelengths. Of the selected particles an observed shift was noted in all of the post-hybridization WGM signals. Note reproducible red shifts in mode profiles resulted when 70 base-oligo-modified particles were hybridized with cDNA concentrations $10^{-7}$ to $10^{-14}$ M, furthermore no consistent peak shifts were evident in the control sample; B) Shifts (Δλ) as a function of cDNA concentration. Error calculations of the peak displacement about $\lambda_{max}$ were calculated as ±0.44 nm; C) Peak position analysis from the same en1 target particle before and after exposure to $10^{-18}$ M concentrated sample of unlabeled complementary DNA. Results indicate each fluorescent peak red shifts after exposure to the attomole concentrated unlabeled DNA probe solution.

Methods
Actyloyl Mediated Conjugation of Oligonucleotide Fragments to Microspheres The raw melamine particles were washed several times in Milli-Q (8000 rpm for 5 s) and stored dry and desiccated at 4° C. under nitrogen. Washed MF particles (2 mg) were weighed in an eppendorf tube. The native surface chemistry of the melamine particles (Gao et al, *Macromolecular Materials and Engineering* 286(6):355-361, 2001) provided a robust conjugation surface to immobilize the single-strand oligonucleotide fragments. By utilizing fragments modified with a 5' acrylic acid (acryloyl) group, particle functionalization was carried out in a single room temperature reaction (Sharmin et al, progress in *Organic Coatings* 50(1):47-54, 2001). Particles were resuspended in fresh PBS followed by the addition of 15 µL of 200 µM acryloyl TMR-labeled oligonucleotides. The reaction was vortexed and gently mixed on a motorized wheel for 1 hr. The coupled microspheres were washed with buffer and pelleted in a microcentrifuge (8000 rpm for 5 s) to remove the supernatant. All oligo-conjugated microsphere preparations were resuspended in 1 mL buffer (2 g of spheres/ Liter) and stored at 4° C. A schematic of the conjugation process is presented in FIG. 10.

Single Particle Microscope Heating Stage Study
i) Microsphere Dilution

Microspheres were initially diluted in a series of four dilutions by taking 1 µL stock microspheres (2 mg/1 mL) and resuspending it in 1 mL of Milli-Q (dilution 1) and vortexing. Then 250 µL of the dilution was resuspended in 1 mL of Milli-Q $H_2O$ and vortexed. This process was repeated with the new dilution three times. A 1 µL aliquot from dilution 3 or 4 would typically contain 1 particle/µL.

ii) Single Microsphere Immobilization

A 1 µL aliquot of dilution 3 was applied to the base of a single micro-well and the number of microspheres within the droplet was monitored. When a one particle count had been established the particles emission spectrum was recorded after the addition of a 49 µL volume of fresh buffer pH 7.0. The melamine particles were immobilized on the base of single micro-well's under the effects of gravity.

iii) Control Buffer-Only and rs10434 Target Probe Assay

The heating stage temperature was increased to 37° C. and allowed to equilibrate for 2 min and then a single spectrum was captured. 5 µL of Milli-Q or a 2 µM target probe solution was then applied to the well. The stage-temperature was increased to 72° C. and held for 2 min followed by spectral acquisition. Finally the stage temperature was decreased to 37° C. or room temperature.

Rs10434 Hybridization Assay Using DNA Fragments from PCR Amplified Control Genomic DNA Samples
i) Hybridization Target Probe Treatment 2 µL of desired target DNA probe (10 ng/µL) solution was applied directly to a well containing a single rs10434-MF target particle. A 5 min hybridization cycle at 90° C. was performed followed by 10 min room temperature cooling cycle. Emission signal scans were acquired after each cycle (×3). Hybridization treatment was repeated for individual 1, 2 and 3 DNA samples. All emission signals were captured in solution and no washing or changing of the reaction buffer was undertaken.

Unless otherwise noted all assays post-target probe exposure treatment were scanned while the microspheres remained immersed in hybridization buffer. The fluorescence excitation and emission signal measurements from treated spheres were captured in solution, typically at 500 ms-2 s integration time when using gridded silica plates and 384 well optical plates. Plates could be stored at 4° C. and microspheres could be successfully employed in further hybridization assays as required.

Particle Development and Characterization Study
Propagating WGMs in Solution

The oligonucleotide fragments used to functionalise the microspheres were designed and constructed to mimic a 30 base strand spanning the rs10434 SNP region of the human genome. The sequence is homologous to the region on chromosome 6. Sequence analysis indicates the region encodes for the vascular endothelial growth factor receptor (VEGF) [Awata et al, *Biochemical and Biophysical Research Communications* 333(3):679-685, 2005; Errera et al, *Diabetes Care* 30(2):275-279, 2007; Joussen et al, *Ophtalmologe* 100(5): 363-370, 2003; Sowers and Epstein, *Hypertension* 26(6): 869-879, 1995; Uhlmann et al, *Experimental and Clinical Endocrinology & Diabetes* 114(6):275-294, 2006]. An extensive BLAST search of the full rs10434 SNP region revealed two matches; the sequence has homologies to 866 bp on the 5' side (vascular endothelial growth factor isoform e precursor), location: 6p12; and 215111 bp on the 3' side: hypothetical protein LOC221416, location: 6p21.1. Individuals with a predisposition in this region have increased susceptibility to Diabetic retinopathy, Diabetes Mellitus, Non Insulin Dependent Diabetes Mellitus also known as Type 2 Diabetes (NIDDM or T2D), Maturity-Onset Diabetes (MOD) and Insulin Resistance. The hyperglycaemia experienced by diabetic patients causes abnormal vascular cell function, in particular in the endothelium at later stages of the disease. These individuals commonly experience progressive degeneration of the micro- and macro-circulation which consequently leads to organ damage (Laselva et al, *Acta Diabetologica* 30(4):190-200, 1993; Ciulla et al, *Acta Ophthalmologica Scandinavica* 80(5):468-477, 2002). Studies have demonstrated that the selected SNP region could potentially be used as a marker for T2D and related illnesses. The findings presented here demonstrate the validity of the optimized WGM platform as an effective diagnostic tool to routinely score known human disease related SNP targets.

The oligo-modified MF particles have a diameter of 7.52 microns and were directly bioconjugated with 5' acryloyl modified TMR labeled target oligonucleotides. There is fluorescence excitation of the particle through a blue multi-line Ar+ laser at a 350 µW excitation power through a 550 nm λ barrier filter. Fluorescence intensity profiling demonstrates the conjugation between the acryloyl DNA fragments and the native —NH groups on the particles surface are robust (Krajnc and Toplak, *Reactive & Functional Polymers* 52(1):11-18, 2002).

Silica Versus Melamine

Figure 11:
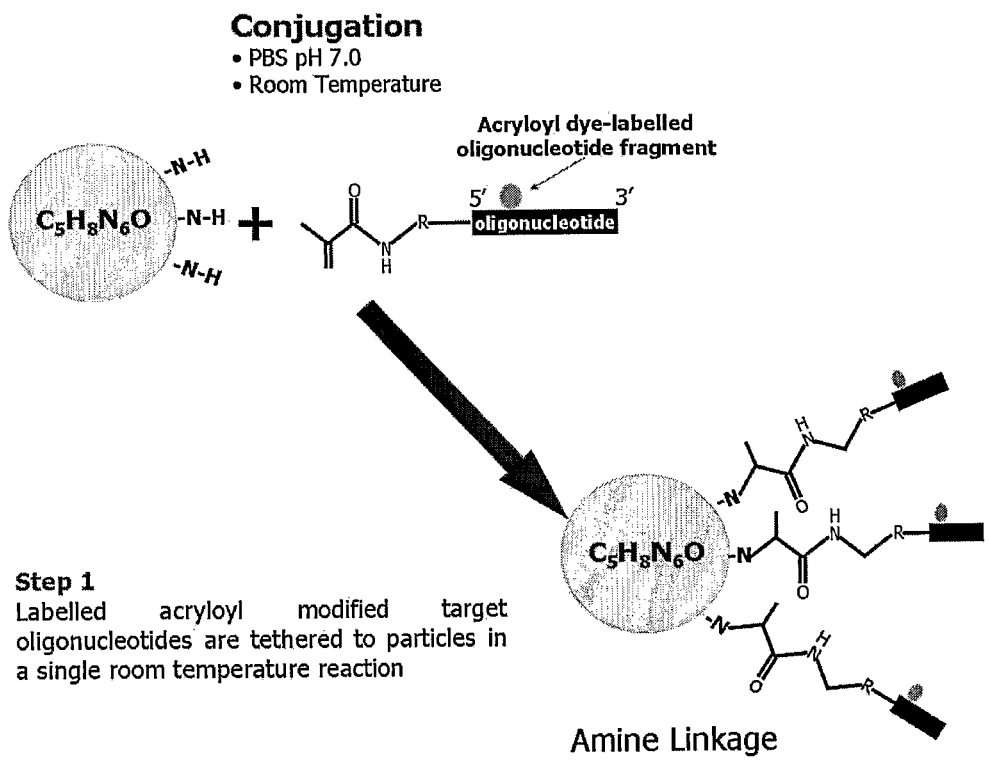
FIG. 11 is a schematic illustration of the reaction chemistry utilized to functionalize raw melamine formaldehyde (MF) particles with labeled single-strand-oligonucleotide fragments. Note the reaction is completed in a single step at room temperature using buffer only. The fragments covalently bind with —NH groups on the particle surface.

With previous silica composite microsphere studies all measurements had to be taken in air. This required evaporation of excess reaction liquid to improve signal emission from a single particle. The major goal of this section was to develop an optimized single particle WGM solution based hybridization assay. The emission signal was measured systematically from an immobilized single MF ($n_r$ 1.68) and silica particle in air and water. Initially the respective emission signals were captured in air then a single droplet of Milli-Q $H_2O$ (R>18 M Ωcm) was administered onto each immobilization plate to completely immerse the particles. Gallery mode signals were acquired from relocated spheres in water and air after repeating the process several times. FIG. 11 demonstrates a typical output following the outlined treatments. For the silica microspheres each water treatment resulted in dissipation of emission signal peaks and the captured signal resembled that of free TMR in aqueous media [Nuhiji and Mulvaney, 2007 supra] (blue and red spectra). However, following evaporation of the Milli-Q the characteristic WGM emission profile re-developed FIG. 11A (black, green and aqua blue spectra). A broadening and loss of modes in conjunction with a decrease in mode intensity occurred when the melamine particles were exposed to Milli-Q; however, several well-defined peaks could still be reproducibly collected (FIG. 12B red and blue spectra). As the MF particles were the main focus of this research from this point on, the baseline spectra are also provided in panels C) and D) of FIG. 11.

Micro-Well Plate Assay

Figure 4:
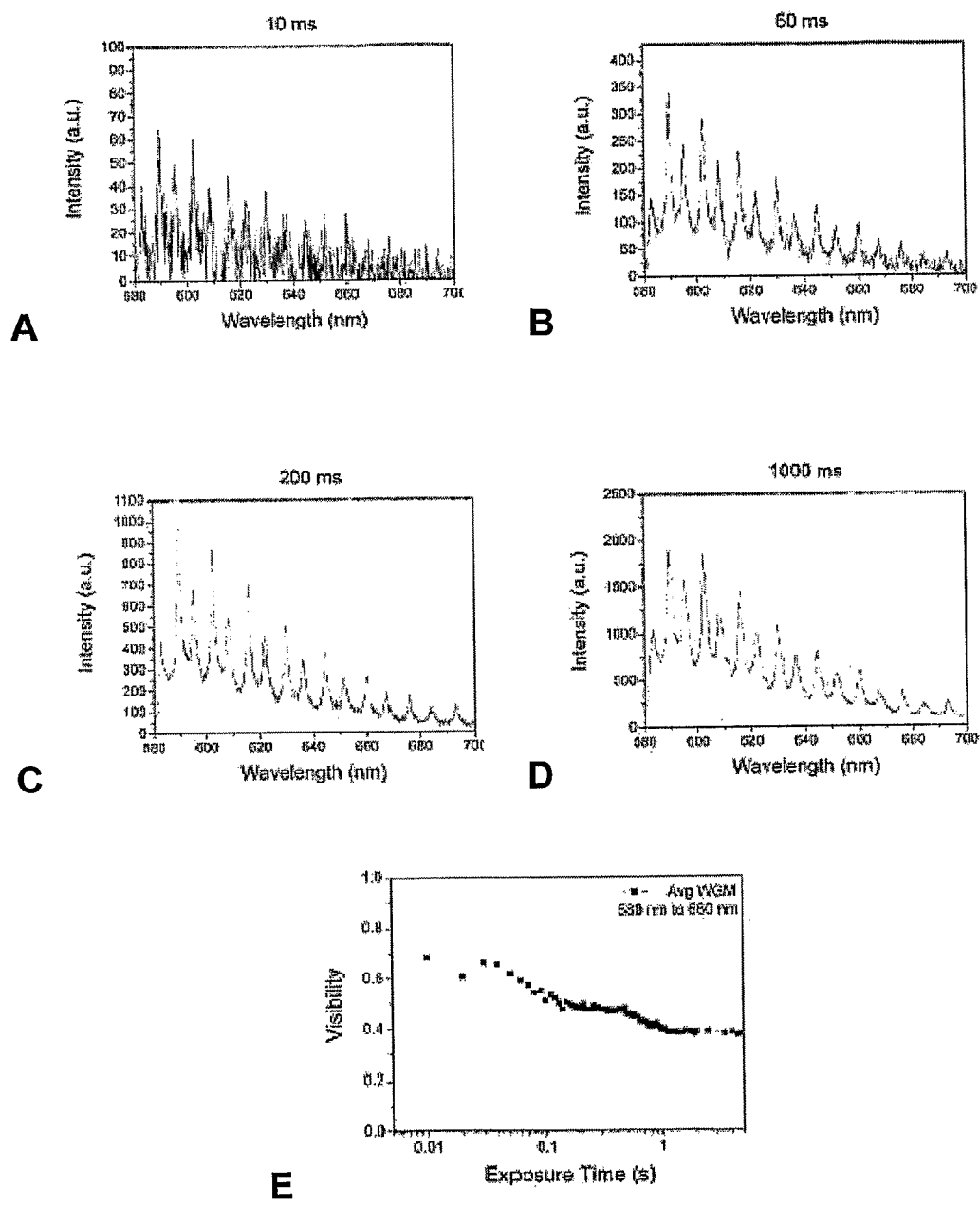
FIG. 4 is a graphical representation of WGM profile generated following illumination of microspheroidal particles with incident light (532 nm, 50 μW) for 10, 60, 200 and 1,000 ms (A, B, C and D, respectively). Visibility decreased gradually up to 5 seconds exposure time (E).
Figure 12:
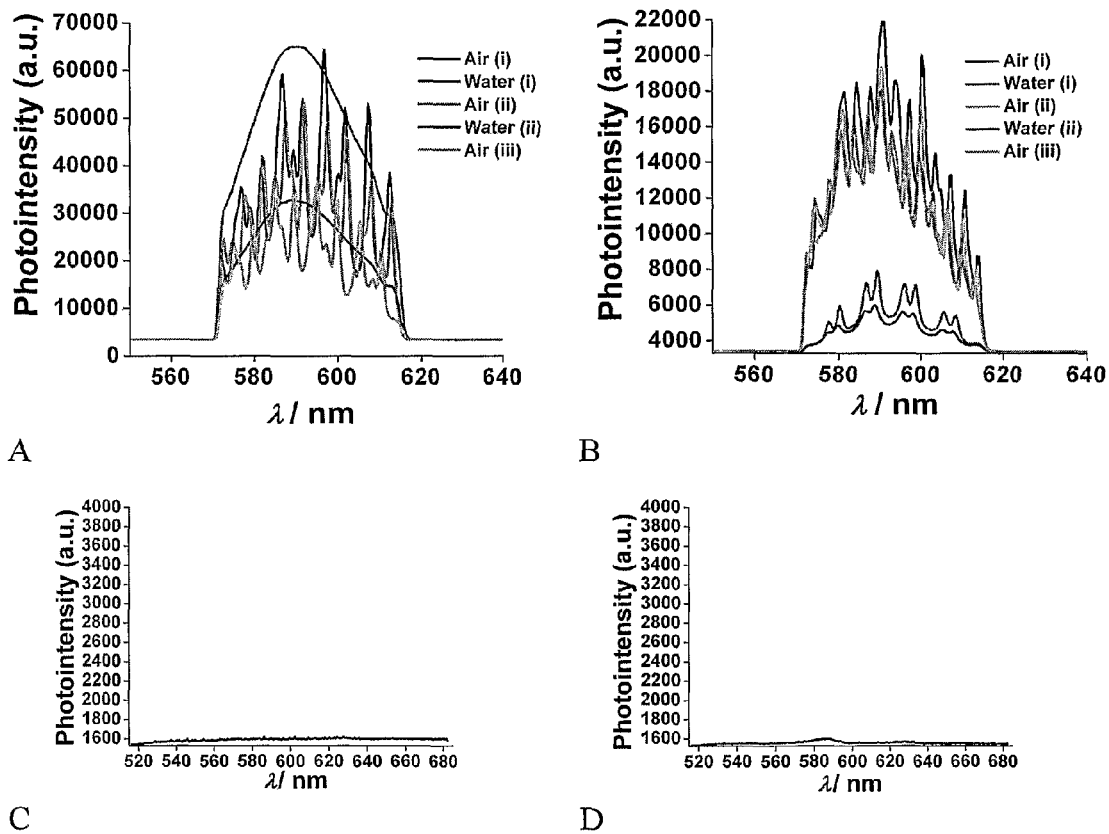
FIG. 12 is a graphical representation showing particle excitation was achieved through an 80 W mercury lamp and a 420-490 nm filter block. Emission signals captured in air and water from 7.50 μM 30 base (TMR) oligo-modified microspheres. A) Silica; B) Melamine. Microspheres were immersed in a singlet droplet of Milli-Q and spectrally analyzed, and water was evaporated off before scans were taken in air. Note that in the excited melamine particle example following the addition of water a WGM emission signal could still be observed. The baseline spectra acquired from a single 7.52 μm MF particle prior to oligonucleotide functionalization, through a 2 s integration using a TRIAX 550 spectrometer (±0.05 nm); C) Air; D) Solution (Mill-Q $H_2O$).
Figure 13:
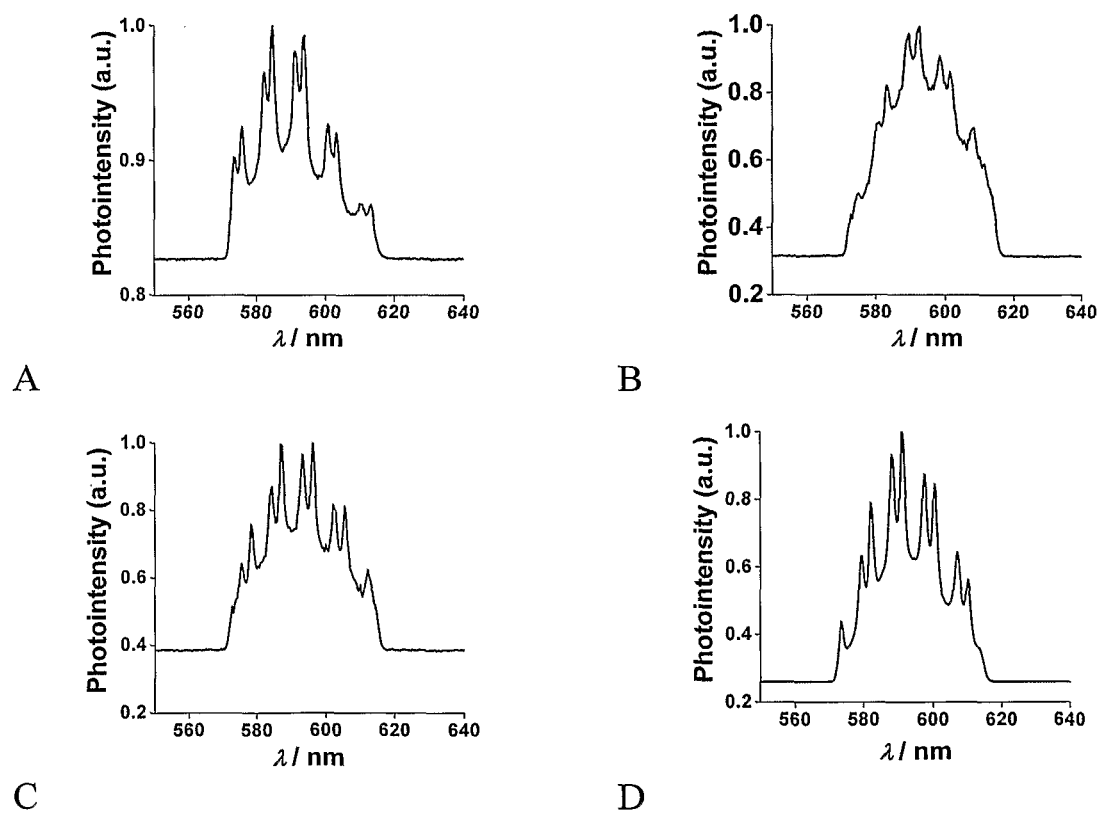
FIG. 13 is a graphical representation showing emission signal measurements, taken using assay plates derived of several composite materials; Particle excitation was achieved through an 80 W mercury lamp and a 420-490 nm filter block. A) Silica gridded array plate; B) Polymer based 96 well cell-culture plate; C) Polycarbonate 384 cytowell plate; D) 384 well optical grade micro-titre plate.

The MF particles ability to support a WGM in solution led to the next investigation, which was to select a hybridization substrate which facilitates routine acquisition of relatively high-Q WGMs in solution. Presenting the particles in a micro-titre plate format moves a step closer towards the direction of a high throughput automated assay. The analysis was based on WGM signal quality that could be collected from the oligo-modified MF particles while immobilized on a micro-well and assay plate substrate. Modified MF particles were immobilized on a silica gridded array plate, within a single well 384 well polycarbonate cytoplate, 384 well optical plate and a 96 well polymer cell culture plate. Emission signals were collected from selected particles while immersed in standard hybridization buffer. FIG. 12 illustrates a representative emission profile obtained using each selected substrate. Due to the small working width of the substrate it was expected that the silica gridded array would produce high signal outputs from a selected MF particle (FIG. 12A). However for a high throughput format, a well-based system was the desired direction. The first micro-plate system analysis was carried out with a common plastic based 96 well culture plate (FIG. 12B). The collected emission signal indicates a WGM profile consisting of several broad low intensity peaks. This was simply due to a large width of the base of each well and to the fact that plastic has high scattering properties. Also the use of a lower objective magnification power (×40) to allow for a large working distance reduced the overall signal. However, the transparency of the material allowed for easy imaging and location of the particles. Using lenses with larger working distances is governed by a trade-off, as an increase in working distance is directly associated with an increase in signal loss. Next a 384-well CC3-trademark polystyrene/polymer base plate was analyzed which mimics Poly-D-Lysine using a sterile, non-biological coating. The coating is positively charged and promotes the adhesion of weakly adhesive cells and in our case would aid in the immobilization of the negatively charged oligo/DNA coated 7.52 micron MF particles. Each well had a smaller total working volume (polymer based plate: base width 100 µm; well area, 0.05 $cm^2$/well with a total working volume, 120 µL/well). Also the flat bottom well geometry and visible transparency allowed easy access to the plate and manipulation using the microscope X/Y oriented working stage. FIG. 12C shows an example of a typical emission signal from an MF particle. Present are a series of identifiable narrow, high intensity fluorescent peaks. A 384 optical plate was also employed with the same working dimensions and volumes as the polymer plate. However, the base width was narrower (50 µm) and the well base did not hold a positive charge. Nine distinct emission peaks are noted within the WGM profile as indicated in FIGS. 13A and C. The particle spectrum acquired through the 384 well optical grade plate indicated the intensity of each identifiable mode was improved (FIG. 12D) in comparison to the spectra in panels A-C. The doublet effect at each $\lambda_{max}$ noted in the WGM outputs presented in FIG. 4 is simply an effect of WGM signal acquisition in solution.

Heating Effects

Figure 14:
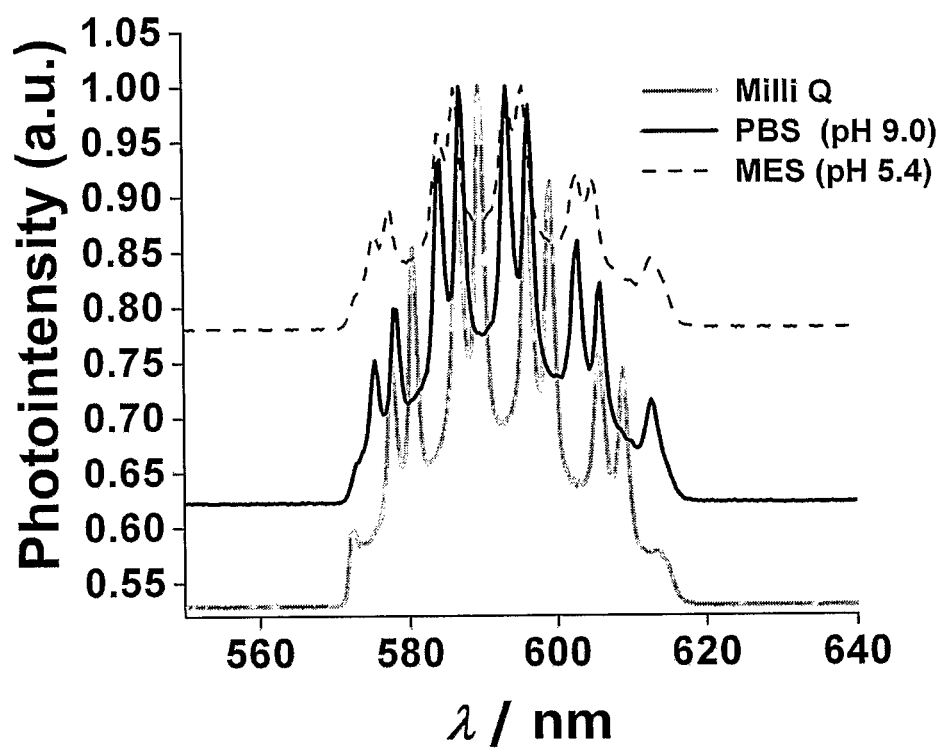
FIG. 14 is a graphical representation showing heat stability analysis of oligonucleotide (TMR) functionalized 7.52 µm MF particles. Particles were immersed in solution under constant heat at 90° C. over a 3 hr period in Milli-Q, Buffer or MES (pH 5.4). A WGM was collected from each test particle utilizing an 80 W mercury lamp and a 420-490 nm filter block. Note the selected particle heated in MES exhibits a marked reduction in its WGM emission signal (dotted spectra) relative to the selected PBS treated (black Spectra) and Milli-Q treated (grey spectra) oligo-modified MF particles.

The advantage of presenting the MF-particles in a micro-well format in a working assay has therefore been established. However, during a DNA hybridization reaction the microspheres can be exposed to extreme reaction conditions >90° C. Particle functionalization with the acryloyl oligonucleotide fragments remains intact when reacted under mild conditions (<37° C.). However, it was yet unknown how excessive thermal stress would effect the conjugation. Using a 384 well optical micro-well plate a heating study was developed to determine the resilience of the chemical bond at elevated temperatures. Single MF particles were immobilized into micro-wells and then immersed in buffer, MES (pH 5.4) or Milli-Q $H_2O$ (control). The reference photoluminescence (PL) signal was measured from selected particles and the plate was heated to standard hybridization assay temperature (90° C.). The temperature was maintained for three hours during which time the selected particles were relocated and the emission signal regularly collected. FIG. 14 presents normalized WGM spectra acquired from the selected particles after 3 hours of heat exposure. Over the 3 hr period the greatest effect was noted in the particle immersed in MES (black dashed line) which exhibited a significant loss of PL signal compared with particles immersed in hybridization buffer (black solid line). The strongest signal following heat treatment was observed in the control particle which was maintained in Milli-Q only (grey solid line). The emission signal level did vary between samples. However, a clear WGM profile with several identifiable peaks could still be obtained from each particle after 3 hrs heating.

Figure 15:
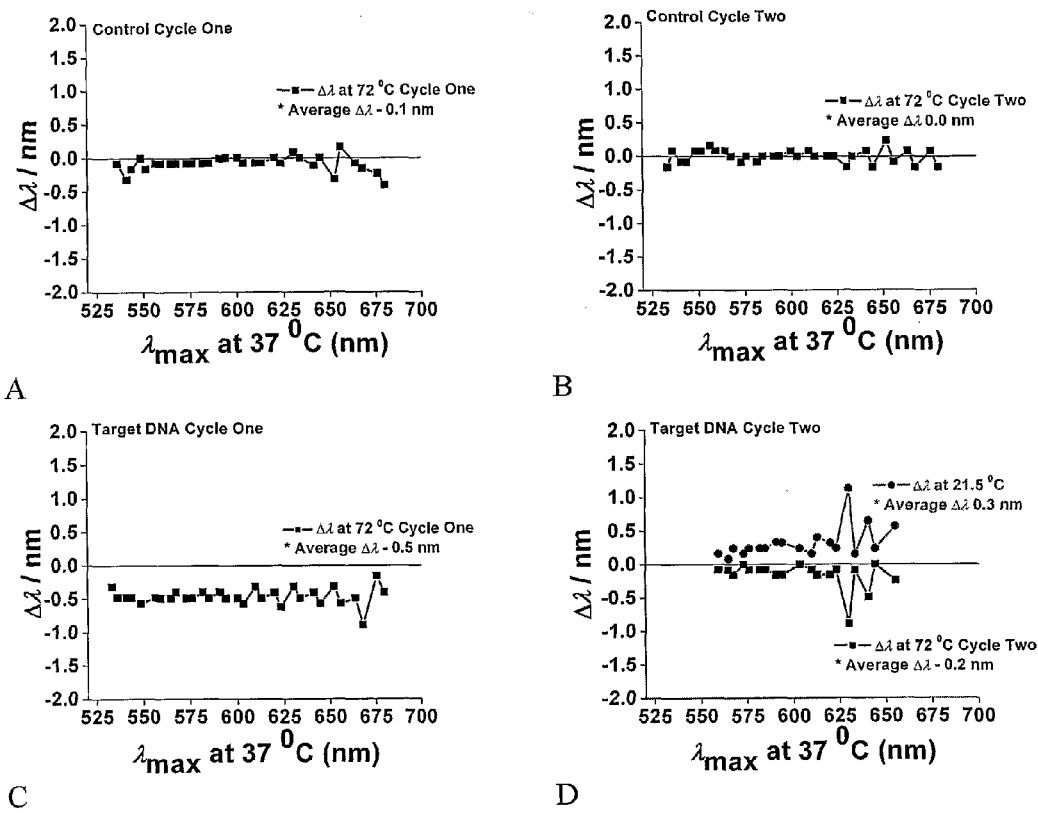
FIG. 15 is a graphical representation showing thermo-cycled hybridization binding study. A tow-step temperature gradient (37° C.-72° C.) was created using a thermo-regulated microscope stage coupled to the confocal/TRIAX setup. The target DNA ($T_m$ 71.2° C.) was complementary to the rs10434 target fragments attached to the particle. Hybridization cycles were completed on a single microsphere with Milli-Q H$_2$O (control) and target DNA. A fluorescence signal was captured at each temperature gradient and the $\Delta\lambda$ was observed. A) Control hyb-cycle one; B) Control hyb-cycle two; C) Target probe hyb-cycle one; D) Target probe hyb-cycle two. All fluorescent peaks blue-shift at maximum cycle temperature (72° C.) [only when target DNA is present] and red-shift when stage temperature was <target probe $T_m$.

The characterization experiments carried out demonstrated that the particles described in this Example can support WGMs in solution. Next, a Linkam PE100-NI thermo-controlled microscope stage was employed to investigate 'real-time' WGM signal perturbations in a micro-well solution-based hybridization assay. An assay was developed utilizing the stage-set-up to determine if thermal changes to the local medium around a microsphere above or below the $T_m$ of a hybridized complementary probe could be detected cyclically. The constructed 30 b target probes labeled as α-rs10434 A ($T_m$ 71.2° C.) were complementary to the fragments tethered to the MF particles. A single 7.52 μm MF-rs10434 target particle was cycled through a two-step gradient (37° C.-72° C.). An initial hybridization reaction was completed following the addition of 5 μL of Milli-Q. Spectra acquired at a 2 s integration time at each gradient temperature through several cycles indicated no consistent movement of the WGM peaks FIG. 15A-B. Using the same particle the experimental conditions were repeated with addition of the target probe DNA (5 μL of a 2 μM stock). After an initial, hybridization cycle the acquired emission signal data showed that exposure to α-rs10434 A fragment solution at 72° C. resulted in a blue shift of the major WGM peaks and a decrease of the stage temperature to 37° C. red-shifted the same peaks (FIG. 15C). A repeated hybridization cycle resulted in consistently observed red-shifts of the WGM peaks when the local-plate temperature was less than the target probe $T_m$ and blue-shifted when temperature was increased to greater than the target probe $T_m$ FIG. 15D-E.

Human Genome Target Assay

Using control gDNA acquired from three individual controls (healthy individuals) DNA fragments of approximately 20 bases were amplified using primers which spanned the rs10434 SNP region. The genotypes of the above individuals were determined using the Sequenom MassARRAY genotyping platform. Each individual had a different genotype. Individual 1 was homozygous for the A allele (A/A), individual 2 was heterozygous (A/G) and individual 3 was homozygous for the G allele (G/G) at this locus. The aim here was to determine whether a single base pair difference could be detected from the PCR amplified samples using the WGM system. A single rs10434-MF particle specific for the A allele of the rs10434 DNA variant was immobilized in a micro-plate well; the particle was then exposed to the 3 different analytes over separate hybridization reactions. Each hybridization was completed at 90° C. for 5 min after a 2 μL addition of the DNA sample (Individual 1-3). Emission signals were collected after each hybridization reaction respectively after the reaction temperature gradient had been decreased to ambient room temperature. WGM signatures acquired after each treatment relative to the reference signal (black spectra) were determined. The peak positions were analyzed relative to the un-treated WGM profile and the Δλ noted. The spectra obtained show the peak wavelength positions as a function of the peak-shift about the given reference wavelength. A positive red-shift of all the major fluorescent gallery modes resulted after exposure to sample Individual 1 (black solid-squares). The same particle was then treated with Individual 2 DNA sample. The WGM signal acquired post exposure indicated a red-shift of all fluorescent peaks (compared with the untreated signal). However, relative to the wavelength peak positions post treatment with Individual 1 sample, treatment with the heterozygous individual 2 sample caused a blue-shift of the fluorescent modes. Final treatment with DNA from Individual 3 (green-solid triangles) then resulted in another blue WGM shift relative to the mode signature acquired post treatment with amplified DNA from Individual 1. These very small observed blue shifts are the result of the introduction of the mismatched DNA probes from Individual 2 and 3. These probes non-specifically bind and as a result decreased the number of binding sites available for the matched DNA from Individual 1.

Target Discrimination

To confirm the modified microspheres can routinely discriminate a single base mismatch in a working assay, two lab-synthesized target DNA probes were constructed with a free-internal-amine for dye molecule attachment. The first target (α-rs10434 A) was designed to mimic the [A] rs10434 allelic variant, the fragments were fluorescently tagged with TMR. The alternative analyte contained a single base mismatch and was identified with Bodipy 630/650. Single unlabeled rs10434 target MF particles were immobilized into three micro-wells of a 384 optical plate. Prior to target probe exposure a base line emission signal was taken in solution (buffer) from the selected particles. Two individual assays were completed with the α-rs10434 A and the α-rs10434 B target probes over individual hybridization cycles. The results show a hybridization of the α-rs10434 A target probe. The acquisition of a sharp fluorescent WGM emission signal was verified with a fluorescence intensity image scan taken of the same particle which shows a spherical fluorescent particle. A weak fluorescence WGM signal was acquired from the particle exposed to α-rs10434 B containing the single mismatch however, a fluorescence intensity image scan showed no detectable fluorescence. Exposure of a single particle to both target probes resulted in a blue shift of all major fluorescence gallery mode peaks post α-rs10434 B treatment, if the particle was initially exposed to α-rs10434 A target fragments.

Single particle studies in a serial volume dilution also demonstrated that these oligo-functionalized polymer particles can detect attomole levels of analyte DNA. Such detection volumes highlight the effective use of small reaction volumes to complete an entire single particle hybridization assay. Furthermore, this demonstrates the particles can routinely detect sub-picomolar concentrations of target probe DNA.

Discussion

The results presented here clearly demonstrate non-covalent binding of complementary strands of DNA to the oligo-nucleotide-modified MF microspheres can be detected in solution. The wavelength shifts of the fluorescent gallery modes can be employed to routinely detect the adsorption and desorption of unlabeled complementary DNA fragments under various reaction conditions.

The native surface of the MF particles facilitates conjugation of a dense monolayer of acryloyl modified oligonucleotide fragments. The conjugation is essentially the covalent linkage of a melamine molecule with an acrylic acid. The oligonucleotide modified particles are highly resilient when exposed to high pH solutions at elevated temperatures (90° C.) as high quality WGM signals can be collected from the particles after prolonged exposure. Data demonstrate that FITC labeled human α-IgM antibodies can also bind effectively to the un-modified MF particles. These particles can then be utilized in antibody-antigen binding assays.

DNA has a higher refractive index in the single-stranded (denatured) conformation (Parthasarathy et al, *Applied Physics Letters* 87(11):113901-3, 2005). In its native form the refractive index of DNA is similar to that of typical organic polymers (Samoc et al, *Chemical Physics Letters* 431(1-3): 132-134, 2006). Naturally double-stranded DNA exists as a dielectric material, and alternatively in the denatured form it becomes a semiconductor with a band gap of a few hundred milli-electronvolts (Rakitin et al, *Physical Review Letters* 86(16):3670, 2001). Thus, the WGM shifts described in this Example (post-hybridization) are governed by a decrease or increase in the relative refractive index at the microsphere surface in direct association with an increase in the microspheres diameter (Niu and Saraf, *Smart Materials and Structures* 11(5):778-782, 2002). How these parameter(s) influence the WGM specifically is yet to be elucidated, however in contrast the characteristic shifts are routinely reproducible using both composite particles.

These single particle studies demonstrate that during a hybridization assay the Δλ shifts in a WGM signal acquired from rs10434 modified particles can be used to discriminate a single base change in lab-synthesized probe DNA. When the particles are presented in a micro-plate format the consistent peak shifts are confirmed in an automated system using PCR amplified gDNA containing the region expected to contain the single nucleotide change of interest. The MF rs10434-target particles described in this Example can discriminate between various alleles of the diabetes-related rs10434 SNP (≅100b). The position of the fluorophore at the first nucleotide base of the tethered acryloyl oligonucleotides (approximately 5-10 nm from the colloid surface), facilitates the routine total-internal-reflection of the excited light in air and water mediums.

The ability to excite WGM in solution in a micro-well format assay completely avoids problems encountered with the system described in Examples 5 and 6. A system utilizing a micro-well format decreases the running time to complete an assay, as particles are located rapidly and no wash steps are required. Ultimately this format enables an entire assay to be performed on the same particle routinely in solution, which also provides an organized system for the re-employment of the sensors for further testing.

Furthermore, the system described in the current Example does not utilize optic-fibre coupling methods to excite a WGM which drastically simplifies the assay. Attomole volumes of target DNA probe solution can be routinely detected. The cyclically reversible WGM shifts observed in the MF microspheres importantly indicates the particles can be recycled. The WGM peak shifts were shown to be reversible when the local temperature was oscillated above and below the $T_m$ of the target probe; hence, the spectral red-shifts are specifically due to hybridization of complementary DNA. The binding affinity of a target probe is significantly decreased when a DNA fragment has a single base mismatch. Non-specific binding, although found to be negligible can cause small blue-shifts in a particle's WGM spectra if the same particle is initially exposed to a complementary target. In a single-well-single-particle hybridization reaction the compared WGM emission spectra indicate a specific target probe has a far greater binding affinity as opposed to a fragment containing a single base mismatch.

These findings show that high-refractive index melamine particles modified with labeled (30 base) oligonucleotide fragments routinely emit WGM in solution. When the particle is excited in solution, the excitation signal does decrease in photoluminescence intensity and the fluorescent modes broaden. However, a series of well-defined WGM resonance peaks can still be routinely identified.

EXAMPLE 8

Optimal Conditions for Whispering Gallery Mode Excitation, in Single Fluorescent Silica and Melamine Oligonucleotide Modified Microspheres This Example reports on the development of a series of optimized parameters to routinely excite high quality whispering gallery modes (WGM) in the fluorescent colloids. The target specific oligonucleotide-modified (TSOM) silica and melamine microspheres (7.50-7.52 μm) [Microparticles Germany GmbH] presented in Examples 5 to 7 are utilized throughout.

Experimental Section
Materials

Materials and methods employed for particle synthesis, immobilization strategies and WGM characterization are as described in Examples 5 to 7.

Whispering Gallery Mode Excitation Parameter Investigation
Coupling Position Effects Using the confocal set-up, an angle-resolved spectroscopic technique was designed to characterize the WGM emission as a result of altering the laser excitation position. Cover glass array slides were prepared with TSOM silica and MF particles as prescribed previously (Examples 5 to 7). The confocal system employed was utilized to alter the excitation position around the circumference of the particle using the acquired particles' transmission image as a reference. At a 350 μW radiation power selected particles were excited through a multi-line Ar+ laser. The emission spectra were collected at a 2 s integration time. For all confocal work herein an Ar+ laser was used for particle excitation. The excitation position was altered at 45° increments over a 360° rotation around the microspheres peripheral boundary relative to the 0° (reference) co-ordinate. When a particle's WGM is excited on the confocal set-up the excitation position 0° is normally utilized, this results in the routine acquisition of high quality WGMs. However, excitation at the selected positions through 360° also results in the collection of strong WGM spectra. Analysis of the spectra-set for the selected example demonstrates no detectable peak shifts are observed for the selected excitation positions (within the spectral resolution of the Triax 550 spectrometer ±0.05 nm). In some cases a peak distortion can occur. The distortion was consistently observed in each WGM spectra acquired at the given wavelength.

A selected MF particle was then scanned in air under the same conditions. Analysis of the WGM spectra-set demonstrates that relative to the 0° spectra, detectable peak shifts are observed (spectral resolution of the CCD ±0.05 nm. Blue shifts are observed in the selected example, however, it is unlikely the particles refractive index has changed to cause the observed shifts. These effects could be due to the movement of the excitation position but are more likely the result of reaching the threshold limits of the CCD. The total internal reflection of light through a TSOM-MF particle immobilized in solution was demonstrated in Example 7. A single MF particle immersed in solution was then excited at the selected radial positions. All fluorescent peaks within the scan range (relative to the 0° scan) consistently red-shift. Results indicate the peak displacement relative to the 0° scan was significantly larger compared with the air results. The increased peak variation is likely attributed to the high light-scattering properties of water. Peak position variation was noted to be highest at positions 180°, 270° and 315° (up to 0.89 nm). These results suggest a fixed excitation position should be utilized for WGM excitation in the TSOM particles.

Repeated Excitation Study

The follow up investigation involved an analysis of the effects caused by the repeated excitation of a TSOM particle through a single position and as a result observe the relative deterioration of the WGM signal. During a single particle hybridization assay a single excitation point (0°) is utilized for all WGM spectra. The importance of using a fixed excitation position has been demonstrated. Importantly this would improve the peak variations.

Routinely a single TSOM-microsphere is excited (scanned) approximately 2-5 times during a working assay. It is important that a microspheres WGM signal remains stable during this time so a set of WGM spectra can be acquired after several treatments. Hence the purpose of this experiment was to determine fluorescence signal deterioration levels associated with the TSOM particles described in this thesis.

Air WGM Deterioration Study

The particles were immobilized on cover glass arrays, the substrates were then mounted on a confocal microscope. Selected silica and MF microspheres were excited in air through the 0° excitation position (integration time 2 s). Spectra set acquired at a 2 s integration time from the selected silica microsphere. The WGM photointensity (PI) significantly decreases in fluorescence intensity after the series of scans. Ten distinct peaks were identified in Scan 1 and 9-10 peaks from the Scan 20.

A single TSOM MF particle was then exposed to the same experimental parameters. The number of identified peaks through scans 1 and scan 20 remained consistent (approximately 16). The Q-factor decreases by a factor of seven and peak position variation is negligible.

Water WGM Deterioration Study

The next step was to repeatedly excite a single TSOM MF particle in solution (Milli-Q $H_2O$). A single particle was lased at position 0° and set of spectra were captured at a 2 s integration time. The number of identified peaks decreased within the selected scan range (eight) in comparison with the air measurements. However, the peak number remained unchanged after the scans were complete (scan 1-20). A six-fold decrease in the Q-factor is observed between scan 1 and 20, respectively.

The scaled spectra collected from the final WGM scans consisted of between 8-16 identifiable peaks. These results demonstrate a WGM profile can be routinely collected (>20) from the same particle after repeated lasing (350 µW radiation power) through a fixed excitation point (0°). Furthermore broadening of peaks due to photodegradation of the TMR dye label and particle immobilization in water, does not result in any significant peak variation. As a result the resilient properties of the particles in a working assay are highlighted.

CCD Resolution

As was demonstrated in the earlier Example, the sensitivity of a spectrometer has an important role in WGM measurements during a working assay. The spectrometer determines the amount of spectral information one can acquire from an excited particle and the sensitivity limits of the WGM detection platform. In this Example, microscope set-ups and sensitivity of the CCD detectors are compared.

A silica particle was first excited (position 0°) in air, and the spectra collected with a Triax 550 spectrometer (spectral resolution ±0.05 nm) at an integration time of 2 s. A spectrum was then acquired from the same particle through a mercury lamp (excitation output power 35.52 mW). A QE6500 Ocean Optics system (spectral resolution ±0.9 nm) at an 2 s integration time was utilized to acquire a spectrum. A clear broadening is observed of several major peaks from the spectra acquired with the QE6500 spectrometer. Furthermore the spectra acquired through the Triax 550 indicates several peaks ($\lambda_{max}$: 577.54 nm, 588.47 nm, 594.35 nm and 599.95 nm) are not present in the QE6500 spectra. The variation in FWHM. ($\lambda_{max}$ PI=1.00) is calculated to be 0.38 nm (Triax) and 0.98 nm (QE6500), respectively. The same measurements were then taken in air with a single TSOM MF particle. The spectrum acquired through the Triax 550 indicates a loss of several peaks results when the QE6500 is utilized for WGM acquisition ($\lambda_{max}$: 578.81 nm, 584.65 nm, 588.07 nm, 597.73 nm and 608.08 nm). The FWHM values Triax (0.72 nm) and QE6500 (1.27 nm) further indicate the difference in spectral quality.

Next a single MF particle immobilized in solution was fluorescently excited and its spectrum captured. Results indicate the spectra taken in water showed no loss of emission peaks following each respective scan. The Triax captured emission spectra indicates a FWHM of 0.81 nm ($\lambda_{max}$ where PI=1.00) and 1.15 nm from the QE6500 spectra. The degree of peak broadening was comparatively less than was measured for the MF and silica particles in air.

These data sets demonstrate high quality WGMs with a greater number of spectral peaks can be acquired when utilizing a high powered CCD. The acquired WGM profiles also contain more spectral information. However, the variability between these spectrometers is significantly improved (approximately 0.24 nm) when measurements are taken in solution.

The WGM peak shift between spectrometers is simply due to the differing sensitivity of the spectrometers. For example the spectral resolution of the instrument defines the accuracy in which a peak position can be measured as a 'true' $\lambda_{max}$. Hence the Ocean Optics system (±0.9 nm) is less accurate in relation to the 'true $\lambda_{max}$' for each observed WGM peak compared with the TRIAX system (±0.05 nm). Therefore based on these conditions it is expected that there will be variability between the WGM response curves.

Bleaching Times

A bleaching threshold of the microspheres was determined while under constant excitation through a fixed coupling position. The bleaching profiles were measured using the confocal characterization set-up. Single particles were lased in air under a continuous wave at 488 nm (Ar+) using an output energy of 350 µW through the excitation point 0°. All bleaching profiles were measured at the back of a 100× objective (NA=1.4). and imaged. The rate of bleaching was observed as a function over time (s) [200 s]. The fluorescence bleaching profiles of the selected particles were collected for 100 particles from the silica (n=100) and MF (n=100) TSOM particles. The bleaching profiles were averaged from each collection of scans. A three exponential fit was applied to fit the averaged data. The averaged bleaching time curve for the silica particles, indicates 60% of the fluorescence dissipates during constant excitation within 0.23 s. A further 31% of the particles fluorescence signal then bleaches after 2.51 s. Finally the remaining 9% of the particles fluorescence bleaches after 26.40 s. For the given silica sample the majority of the particles fluorescence dissipates after approximately 3.30 s. Comparatively the TSOM-MF particles are shown to be more robust. The data indicate 50% of the particles fluorescence signal degrades after 31.10 s. Using the same 3 exponential fit model, the greatest percentage fluorescence signal photo-degrades after 6.28 s, which is a significant improvement compared with the silica TSOM particles.

A considerably high laser power was utilized for particle excitation (350 µW). However the results indicate a fluorescence signal could still be observed after 26.40 s (silica) and 31.10 s (MF) during constant excitation. These bleaching times can therefore be improved by simply decreasing the excitation energy.

Discussion

Spectral variation associated with spectrophotometric resolving precision was demonstrated to be significantly improved by utilizing the TSOM MF particles which support WGMs in solution. This result further demonstrates a lower strength CCD can be successfully employed in a solution based WGM assay without the loss of important spectral information. The slower bleaching time of the MF particles fluorescence further strengthens the role of the polymer particles in a WGM bio-detection platform.

The downstream development of a high throughput, microfluid-based WGM diagnostic unit should utilize high refractive index homogeneous microspheres. An automated scanning unit should present particles in solution in a micro-well format. The unit should also incorporate a laser excitation system similar to those found in flow cytometers and confocal laser scanning microscopes. The particles must be excited through a fixed position to minimize signal variability. Fixing the excitation position or alternatively presenting the particles in a fixed position will alleviate the need to employ expensive objective lenses and high precision imaging software.

EXAMPLE 9

Comparison of WGM Using Silica and Melamine Formaldehyde Particles

Figure 17:
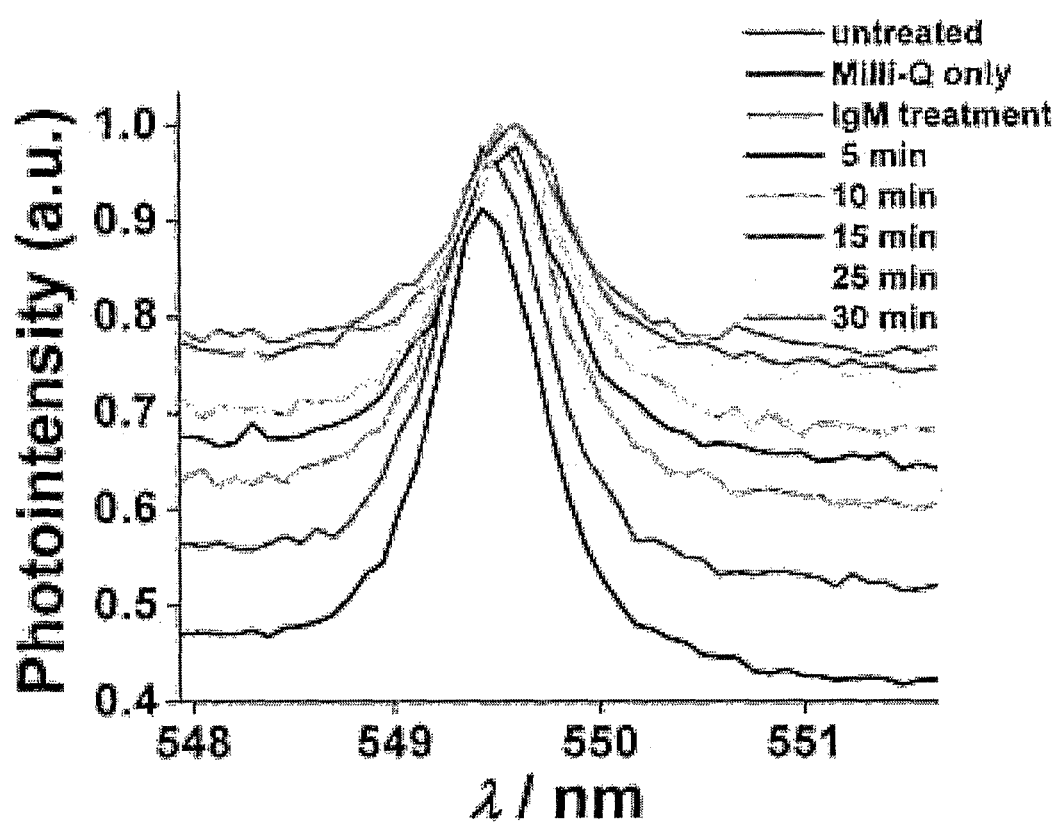
FIG. 17 is a graphical representation of the antibody WGM immuno-assay. A single 7.52 µm MF particle functionalized with a FITC labeled human α-IgM antibody was immobilized in a single micro-well. The entire assay was performed at room temperature. The untreated particle was excited through a Ar+ laser to obtain a reference signal, then treated with Milli-Q followed by unlabeled human IgM. Relative to the untreated WGM, the representative peak-set indicates a typical red shift of several nanometers which resulted following IgM treatment. A minimal shift was noted 30 min after the addition. Spectra were acquired through a Triax 550/CCD confocal setup (spectral resolution ±0.05 nm).

FIGS. 17(A) and (B) show a comparison of the WGM profile obtained using silica particles (B) and melamine formaldehyde particles (A). The solid lines in (A) and (B) were the profiles obtained in air and the dotted lines represent the profiles when the particles were in aqueous media.

Figure 16:
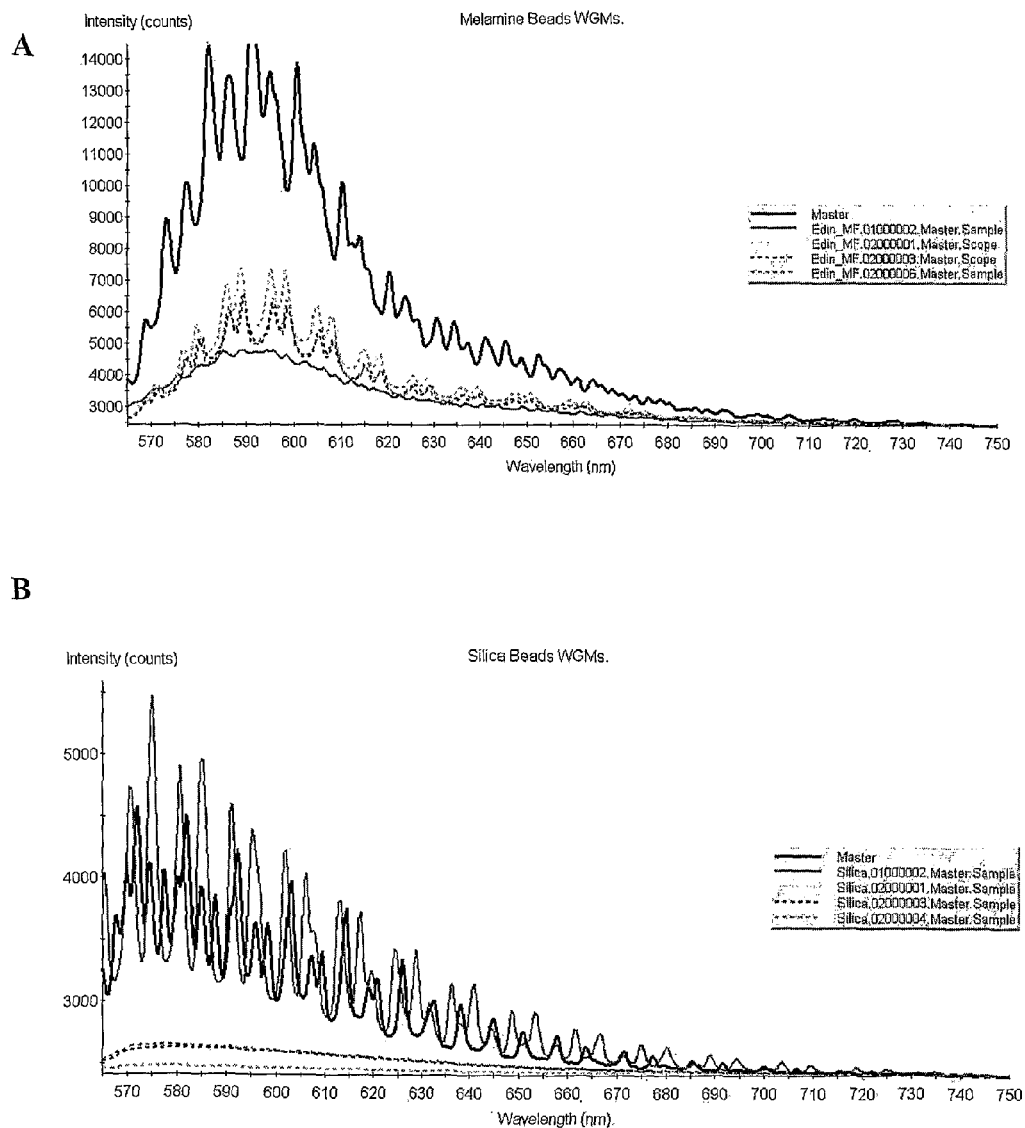
FIGS. 16(A) and (B) are graphical representations showing (A) Melamine beads WGM solid lines: Solid lines are WGM of single melamine formaldehyde beads obtained in air. Spectra acquired in aqueous media are shown in dotted lines; (B) Silica beads WGM: Solid lines are WGM of single silica beads obtained in air. Spectra acquired in aqueous media are shown in dotted lines. Acquisition in water yielded very faint fluorescence and no WGM.

The acquisition in water using silica beads yielded very faint fluorescence but no WGM (FIG. 16(B)). When melamine formaldehyde was used, a strong WGM profile was obtained.

EXAMPLE 10

Immuno-WGM

An immuno-based WGM assay provides a setting for a diagnostic platform. Data demonstrate a fluorescent WGM signal entitled from an antibody (Human α-IgM) modified MF particle can be utilized to discriminate between a control reagent and target antigen (FIG. 17) in a room temperature reaction. The immuno-WGM assay provides an alternative recognition format with tunable specificity to a plethora of biomolecular targets such as proteins, antibodies, animal and plant pathogens, bacteria, interleukins, peptides, RNA, mRNA and prions. Immuno-WGM assay has potential in applications in the food hygiene industry, environmental water testing, agricultural industry, military (biowarfare), virology, microbiology diagnostics and pharmacological screening.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Awata et al, *Biochemical and Biophysical Research Communications* 333(3):679-685, 2005
Battersby et al, *Chemical Communications* 14:1435-1441, 2002
Ciulla et al, *Acta Ophthalmologica Scandinavica* 80(5):468-477, 2002
Corrie et al, *Langmuir* 22(6):2731-2737, 2006
Erickson et al., *Science* 249:527-533, 1990
Errera et al, *Diabetes Care* 30(2):275-279, 2007
Gao et al, *Macromolecular Materials and Engineering* 286 (6):355-361, 2001
Gomez et al, *Small* 1(2):238-241, 2005
Hermanson, *Bioconjugative Techniques*, Sand Diego: Academic Press Incorporated, 785, 1996
Hodgson, *Bio/Technology* 9:19-21, 1991
Johnston et al, *Chemical Communications* 7:848-850, 2005
Joussen et al, *Ophtalmologe* 100(5):363-370, 2003
Krajnc and Toplak, *Reactive & Functional Polymers* 52(1): 11-18, 2002
Laselva et al, *Acta Diabetologica* 30(4):190-200, 1993
Miller et al, *Chemical Communications* 38:4783-4785, 2005
Moller et al, *Applied Physics Letters* 83(13):2686-2688, 2003
Niu and Saraf, *Smart Materials and Structures* 11(5):778-782, 2002
Nuhiji and Mulvaney, *Small* 3(8):1408-1414, 2007
Parthasarathy et al, *Applied Physics Letters* 87(11):113901-3, 2005
Peyrefitte et al, *Mechanisms of Development* 104(1-2):99-104, 2001
Rakitin et al, *Physical Review Letters* 86(16):3670, 2001
Rychlik et al, *Nucl. Acids Res.* 18(21):6409-6412, 1990
Samoc et al, *Chemical Physics Letters* 431(1-3):132-134, 2006
Sharmin et al, *progress in Organic Coatings* 50(1):47-54, 2001
Sowers and Epstein, *Hypertension* 26(6):869-879, 1995
Uhlmann et al, *Experimental and Clinical Endocrinology & Diabetes* 114(6):275-294, 2006
Verhaegh and Vanblaaderen, *Langmuir* 10(5):1427-1438, 1994
Wells, *Methods Enzymol.* 202:2699-2705, 1991

The invention claimed is:

1. A method for detecting an analyte in a medium, comprising the steps of:
   (i) anchoring a multiplicity of ligands to the analyte to a population of fluorophore-conjugated microspheroidal particles comprising melamine formaldehyde;
   (ii) contacting the microspheroidal particles with a negative control sample and determining a baseline spectrum;
   (iii) contacting the microspheroidal particles with a sample putatively comprising the analyte for a time and under conditions sufficient to facilitate a binding event between the analyte and its respective ligand; and
   (iv) subjecting the microspheroidal particles to a whispering gallery modes (WGM)-based assay using a fixed excitation position determined to produce increased peak variation relative to other excitation positions to detect a binding event.

2. The method of claim 1 wherein the micro spheroidal particles are selected to have a higher refractive index relative to the medium in which the detection occurs.

3. The method of claim 2 wherein the microspheroidal particle has a refractive index greater than 1.40.

4. The method of claim 1, wherein the medium is a liquid or gas phase.

5. The method of claim 4, wherein the liquid phase is an aqueous solution, buffer or biological fluid and the gas phase is air.

6. The method of claim 1 wherein the analyte or its respective ligand comprise a molecule selected from the group consisting of: nucleic acid; protein; peptide; antibody; lipid; carbohydrate; bacterium; virus; cell and a small molecule or chemical entity.

7. The method of claim 6 wherein the analyte or its respective ligand comprise a nucleic acid.

8. The method of claim 6 wherein the nucleic acid comprises single-stranded DNA.

9. The method of claim 8 wherein the single-stranded DNA is prepared by digesting double-stranded DNA with a restriction endonuclease and/or an exonuclease.

10. The method of claim 9 wherein the restriction endonuclease is a Type 1 restriction endonuclease.

11. The method of claim 9 wherein the exonuclease is a lambda exonuclease.

12. The method of claim 8 wherein the single-stranded DNA is prepared from an RNA:DNA hybrid molecule.

13. The method of claim 12 wherein the RNA:DNA hybrid molecule comprises DNA hybridized to messenger RNA prepared by reverse transcription.

14. The method of claim 12 wherein the RNA is viral RNA.

15. The method of claim 1 wherein the analyte or ligand is derived from an isolated sample obtained from a biological, industrial, laboratory or environmental source.

16. The method of claim 15 wherein the sample comprises material of mineral, synthetic, eukaryotic, prokaryotic or viral origin.

17. A method for detecting a binding event between an analyte and a ligand, comprising performing the steps of the method for detecting an analyte in a medium according to claim 1, wherein a change in a WGM profile of the fluorophore upon contacting the microspheroidal particle with the sample putatively comprising the analyte is indicative of a binding event between the analyte and the ligand.

* * * * *

SEQUENCE LISTING

<160> NUMBER OF SEQ ID NOS: 12

<210> SEQ ID NO 1
<211> LENGTH: 69
<212> TYPE: DNA
<213> ORGANISM: Artificial sequence
<220> FEATURE:
<223> OTHER INFORMATION: oligonucleotide

<400> SEQUENCE: 1
tatggaatta accctcacta aagggaggac agctatggac tgcttctaca cagtctcctg      60
tacctgggc                                                              69

```
<210> SEQ ID NO 2
<211> LENGTH: 30
<212> TYPE: DNA
<213> ORGANISM: Artificial sequence
<220> FEATURE:
<223> OTHER INFORMATION: oligonucleotide

<400> SEQUENCE: 2
caggagactg tgtagaagca gtccatagct                                    30

<210> SEQ ID NO 3
<211> LENGTH: 41
<212> TYPE: DNA
<213> ORGANISM: Artificial sequence
<220> FEATURE:
<223> OTHER INFORMATION: oligonucleotide

<400> SEQUENCE: 3
gtcctcccct tcaggagact gtgtagaagc agtccatagc t                       41

<210> SEQ ID NO 4
<211> LENGTH: 21
<212> TYPE: DNA
<213> ORGANISM: Artificial sequence
<220> FEATURE:
<223> OTHER INFORMATION: oligonucleotide

<400> SEQUENCE: 4
caggagactg tgtagaagca g                                             21

<210> SEQ ID NO 5
<211> LENGTH: 10
<212> TYPE: DNA
<213> ORGANISM: Artificial sequence
<220> FEATURE:
<223> OTHER INFORMATION: oligonucleotide

<400> SEQUENCE: 5
caggagactg                                                          10

<210> SEQ ID NO 6
<211> LENGTH: 62
<212> TYPE: DNA
<213> ORGANISM: Artificial sequence
<220> FEATURE:
<223> OTHER INFORMATION: oligonucleotide

<400> SEQUENCE: 6
tttaggccta tggacacgtg cggatgattt gcctattccg aatccgcagg atgggcctta   60
ca                                                                  62

<210> SEQ ID NO 7
<211> LENGTH: 30
<212> TYPE: DNA
<213> ORGANISM: Artificial sequence
<220> FEATURE:
<223> OTHER INFORMATION: oligonucleotide

<400> SEQUENCE: 7
ttcgccggga catctgccag tggtctcctg                                    30

<210> SEQ ID NO 8
<211> LENGTH: 30
<212> TYPE: DNA
<213> ORGANISM: Artificial sequence
<220> FEATURE:
```

```
-continued

<223> OTHER INFORMATION: oligonucleotide

<400> SEQUENCE: 8
caggagacca ctggcagatg tcccggcgaa                              30

<210> SEQ ID NO 9
<211> LENGTH: 30
<212> TYPE: DNA
<213> ORGANISM: Artificial sequence
<220> FEATURE:
<223> OTHER INFORMATION: oligonucleotide

<400> SEQUENCE: 9
caggagccca ctggcagatg tcccggcgaa                              30

<210> SEQ ID NO 10
<211> LENGTH: 99
<212> TYPE: DNA
<213> ORGANISM: Artificial sequence
<220> FEATURE:
<223> OTHER INFORMATION: oligonucleotide

<400> SEQUENCE: 10
tggaggattc aggagcctgg gcggccttcg cttactctca cctgcttctg agttgcccag    60
gagagccact ggcagatgtc ccggcgaaga gaagagaca                           99

<210> SEQ ID NO 11
<211> LENGTH: 30
<212> TYPE: DNA
<213> ORGANISM: Artificial sequence
<220> FEATURE:
<223> OTHER INFORMATION: oligonucleotide

<400> SEQUENCE: 11
acgttggatg atgtgtctct tctcttcgcc                              30

<210> SEQ ID NO 12
<211> LENGTH: 30
<212> TYPE: DNA
<213> ORGANISM: Artificial sequence
<220> FEATURE:
<223> OTHER INFORMATION: oligonucleotide

<400> SEQUENCE: 12
acgttggatg ccttcgctta ctctcacctg                              30
```